(12) United States Patent
Thompson

(10) Patent No.: US 6,428,470 B1
(45) Date of Patent: Aug. 6, 2002

(54) IMAGING SYSTEM AND COMPONENTS THEREOF

(75) Inventor: Robert Lee Thompson, Rogers, AK (US)

(73) Assignee: Pinotage, LLC, Fayetteville, AK (US)

( * ) Notice: Subject to any disclaimer, the term of this patent is extended or adjusted under 35 U.S.C. 154(b) by 0 days.

(21) Appl. No.: 09/382,495

(22) Filed: Aug. 25, 1999

Related U.S. Application Data

(63) Continuation-in-part of application No. 09/065,116, filed on Apr. 23, 1998, now Pat. No. 6,007,484, which is a continuation of application No. 08/937,238, filed on Sep. 16, 1997, now Pat. No. 5,762,603, which is a continuation of application No. 08/708,044, filed on Aug. 30, 1996, now abandoned.

(60) Provisional application No. 60/003,802, filed on Sep. 15, 1995.

(51) Int. Cl.$^7$ .................................................. A61B 1/05
(52) U.S. Cl. ..................... 600/173; 600/176; 600/114; 600/121
(58) Field of Search ................................ 600/109, 112, 600/122, 129, 137, 173, 175, 176, 114, 121, 179; 348/65, 66, 82–85, 143

(56) References Cited

U.S. PATENT DOCUMENTS

| | | |
|---|---|---|
| 3,557,780 A | 1/1971 | Sato |
| 3,896,793 A | 7/1975 | Mitsui et al. |
| 3,958,080 A | 5/1976 | Schadler |
| 4,697,210 A | 9/1987 | Toyota et al. |
| 4,718,417 A | 1/1988 | Kittrell et al. |
| 4,727,859 A | 3/1988 | Lia ............................... 128/4 |
| 4,741,326 A | 5/1988 | Sidall et al. |
| 4,791,479 A | 12/1988 | Ogiu et al. |
| 4,819,620 A | 4/1989 | Okutsu |
| 4,855,838 A | 8/1989 | Jones et al. |
| 4,858,001 A | 8/1989 | Milbank et al. |

(List continued on next page.)

FOREIGN PATENT DOCUMENTS

| | | |
|---|---|---|
| DE | 78 33 379 | 11/1978 |
| DE | 91 13080.8 | 1/1992 |
| GM | 78 33 379 | 2/1979 |
| JP | 23 25 24 | 8/2000 |
| WO | WO 96/10947 | 4/1996 |

*Primary Examiner*—John P. Leubecker
(74) *Attorney, Agent, or Firm*—Wolf, Greenfield & Sacks, P.C.

(57) ABSTRACT

In one embodiment, a camera includes an image sensor, a sheath, and a housing. A first end of the sheath is closed to form a cavity to accommodate the image sensor, and the housing is adapted to mate with a second end of the sheath. One of the housing and the second end of the sheath includes at least one tab, and the other of the housing and the second end of the sheath includes at least one slot, the at least one tab being adapted to mate with the at least one slot when the housing is mated with the second end of the sheath to inhibit the second end of the sheath from rotating with respect to the housing. In another embodiment, a camera includes a sheath, an image sensor, and a support. The support, which is at least partially disposed within the sheath, supports the image sensor within the sheath such that the image sensor is rotatable about at least two axes of rotation with respect to the sheath through a range of orientations, wherein an imaging axis of the image sensor is oriented normal to an inner surface of the sheath throughout the image sensor's range of orientations. In another embodiment, a camera includes a sheath, an image sensor, and at least one light. The image sensor and the at least one light are disposed within the sheath, and the at least one light is adapted to generate sufficient heat to prevent condensation from forming on the sheath when the sheath is inserted into a body of a living patient. In addition, an actuation module for use with a camera, a camera module for use in a camera, and a novel bearing ring assembly are disclosed.

15 Claims, 15 Drawing Sheets

U.S. PATENT DOCUMENTS

| | | | | |
|---|---|---|---|---|
| 4,895,138 | A | 1/1990 | Yabe | |
| 4,905,082 | A | 2/1990 | Nishigaki et al. | |
| 4,947,827 | A | 8/1990 | Opie et al. | |
| 4,971,035 | A | 11/1990 | Ito | |
| 4,989,586 | A | 2/1991 | Furukawa | |
| 5,028,997 | A | 7/1991 | Elberbaum | |
| 5,111,288 | A | 5/1992 | Blackshear | |
| 5,166,787 | A | 11/1992 | Irion | |
| 5,217,453 | A | 6/1993 | Wilk | |
| 5,237,984 | A | 8/1993 | Williams, III et al. | |
| 5,243,967 | A | 9/1993 | Hibino et al. | |
| 5,251,613 | A | 10/1993 | Adair | 128/6 |
| 5,253,638 | A | 10/1993 | Tamburrino et al. | 128/6 |
| 5,267,970 | A | 12/1993 | Chin et al. | 604/175 |
| 5,271,381 | A | 12/1993 | Ailinger et al. | |
| 5,290,168 | A | 3/1994 | Cooper et al. | |
| 5,305,121 | A | 4/1994 | Moll | |
| 5,307,804 | A | 5/1994 | Bonnet | |
| 5,308,325 | A | 5/1994 | Quinn et al. | |
| 5,334,150 | A | 8/1994 | Kaali | |
| 5,349,941 | A | 9/1994 | Hori | |
| 5,351,678 | A | 10/1994 | Clayton et al. | |
| 5,368,015 | A | 11/1994 | Wilk | |
| 5,380,291 | A | 1/1995 | Kaali | |
| 5,381,784 | A | 1/1995 | Adair | |
| 5,381,943 | A | 1/1995 | Allen et al. | |
| 5,383,859 | A | 1/1995 | Sewell, Jr. | 604/164 |
| 5,396,879 | A | 3/1995 | Wilk et al. | |
| 5,402,768 | A | 4/1995 | Adair | |
| 5,418,567 | A | 5/1995 | Boers et al. | 348/143 |
| 5,458,132 | A | 10/1995 | Yabe et al. | |
| 5,483,951 | A | 1/1996 | Frassica et al. | |
| 5,489,256 | A | 2/1996 | Adair | |
| 5,508,735 | A | 4/1996 | Mueller | |
| 5,531,664 | A | 7/1996 | Adachi et al. | |
| 5,538,497 | A | 7/1996 | Hori | |
| 5,540,649 | A | 7/1996 | Bonnell et al. | |
| 5,558,619 | A | 9/1996 | Kami et al. | |
| 5,562,602 | A | 10/1996 | Yabe et al. | 600/121 |
| 5,573,494 | A | 11/1996 | Yabe et al. | |
| 5,591,192 | A | 1/1997 | Privitera et al. | |
| 5,617,762 | A | 4/1997 | Kirsch | 348/143 |
| 5,626,553 | A | 5/1997 | Frassica et al. | |
| 5,689,365 | A | 11/1997 | Takahashi | 600/166 |
| 5,737,013 | A | 4/1998 | Williams et al. | |
| 5,879,289 | A | 3/1999 | Yarush et al. | |
| 5,908,294 | A | 6/1999 | Schick et al. | |
| 5,956,077 | A | * 9/1999 | Qureshi et al. | 348/82 |
| 5,989,182 | A | * 11/1999 | Hori et al. | 600/173 |
| 6,147,701 | A | * 11/2000 | Tamura et al. | 348/143 |

* cited by examiner

IMAGING SYSTEM AND COMPONENTS THEREOF

This application is a continuation-in-part of application Ser. No. 09/065,116, filed Apr. 23, 1998, now U.S. Pat. No. 6,007,484, which is a continuation of application Ser. No. 08/937,238, filed Sep. 16, 1997, now U.S. Pat. No. 5,762,603, which is a continuation of application Ser. No. 08/708,044, filed Aug. 30, 1996, now abandoned, which claims the benefit of provisional application Ser. No. 60/003,802, filed Sep. 15, 1995.

BACKGROUND OF THE INVENTION

1. Field of the Invention

The present invention is directed to the field of optical imaging.

2. Discussion of Related Art

Optical imaging systems are used in a wide variety of applications. For example, optical imaging systems are used for surveillance and/or security in residential, commercial, and military settings. In the medical field, endoscopic optical imaging systems can be used for performing surgical and diagnostic procedures inside the body. Optical imaging systems can also be used in conventional photographic applications, such as still photography or video recording.

In a conventional optical imaging system, the portion of the imaging system that receives light from a target being viewed by the system is physically disposed next to other portions of the imaging system that store, process, or display the image of the target. For example, in a conventional surveillance/security system, a lens, a charge coupled device (CCD) camera, and other electronic components (such as an amplifier, an image processor, etc.) are all disposed within the same camera housing. Other portions of the imaging system (e.g., image storage and/or display) may also be disposed in the camera housing, or may be disposed in a remote location that is connected to the camera housing via cables. Because much of the optical imaging system is disposed within the camera housing, the camera housing is relatively large, heavy, and obtrusive.

In the medical field, due to the small size requirements imposed by invasive surgical and diagnostic procedures, most endoscopic optical imaging systems include an assembly of optical fibers and a lens that is inserted into the patient. The assembly of optical fibers and the lens relay light received from the target to the rest of the system (e.g., a CCD camera, amplifiers, an image processor, an image storage device, a display, etc.) located outside of the patient. Although this arrangement permits the portion of the optical imaging system that is inserted into the patient to be quite small, such optical fiber-based imaging systems are expensive to purchase and maintain.

SUMMARY OF INVENTION

One aspect of the present invention is directed to, a camera including an image sensor, a sheath, and a housing. A first end of the sheath is closed to form a cavity to accommodate the image sensor, and the housing is adapted to mate with a second end of the sheath. One of the housing and the second end of the sheath includes at least one tab, and the other of the housing and the second end of the sheath includes at least one slot, the at least one tab being adapted to mate with the at least one slot when the housing is mated with the second end of the sheath to inhibit the second end of the sheath from rotating with respect to the housing.

Another aspect of the present invention is directed to a camera including a sheath, an image sensor, and a support. The support, which is at least partially disposed within the sheath, supports the image sensor within the sheath such that the image sensor is rotatable about at least two axes of rotation with respect to the sheath through a range of orientations, wherein an imaging axis of the image sensor is oriented normal to an inner surface of the sheath throughout the image sensor's range of orientations.

Another aspect of the present invention is directed to an actuation module for use with a camera including an image sensor that is rotatable about at least two axes of rotation. The actuation module includes a module base, and a pair of actuators. The module base is adapted to be removably mounted in the camera. The pair of actuators is mounted to the base so that the pair of actuators can be removed from and inserted into the camera as a single unit, each of the pair of actuators being adapted to rotate the image sensor about a respective one of the at least two axes of rotation.

Another aspect of the present invention is directed to a camera module for use in a camera. The camera module includes a module base, an image sensor, a cable, and a signal conditioning circuit. The cable is coupled to the image sensor, and the signal conditioning circuit is coupled to the cable to receive an electronic signal produced by the image sensor via the cable. Each of the image sensor, the cable, and the signal conditioning circuit is mounted to the base, and the base is adapted to be removably mounted in the camera, whereby the image sensor, the cable, the signal conditioning circuit, and the base are removable from and insertable into the camera as a single unit.

Another aspect of the present invention is directed to a camera including a sheath, an image sensor, and at least one light. The image sensor and the at least one light are disposed within the sheath, and the at least one light is adapted to generate sufficient heat to prevent condensation from forming on the sheath when the sheath is inserted into a body of a living patient.

Another aspect of the present invention is directed to a bearing ring assembly including first and second rings, and a plurality of ball bearings. The second ring is arranged concentrically with the first ring, and the ball bearings are disposed between the first and second rings such that the first ring is permitted to rotate with respect to the second ring. The first ring includes at least one first mating feature adapted to engage a first structure so that the at first ring is inhibited from rotating with respect to the first structure.

DETAILED DESCRIPTION

Figure 1:
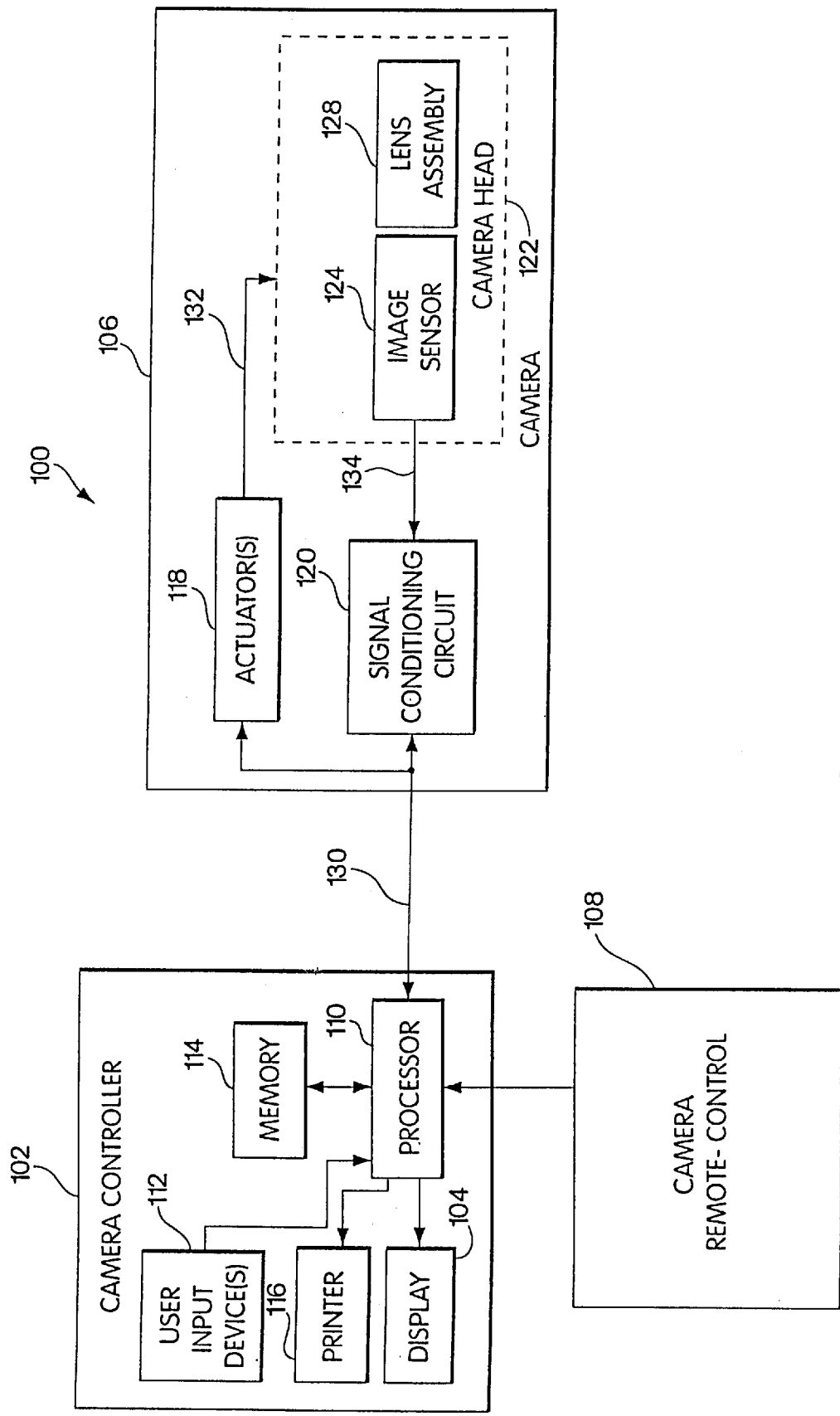
FIG. 1 is a block diagram showing an example of an imaging system configured in accordance with one embodiment of the present invention.

FIG. 1 shows an example of an imaging system 100 according to one embodiment of the present invention. As shown in FIG. 1, the imaging system 100 includes a camera controller 102 (including a display 104), a camera 106, and a camera remote-control 108.

In the illustrative embodiment of FIG. 1, the camera 106 includes a camera head 122 (including an image sensor 124 and a lens assembly 128), a signal-conditioning circuit 120, and one or more actuator(s) 118. In operation, an optical image viewed by the camera head 122 is focused by the lens assembly 128 onto the image sensor 124, and the image sensor 124 converts the received image into electrical signals which are transmitted to the signal conditioning circuit 120 via a connection 134. The signal conditioning circuit 120 processes the signals received from the image sensor 124, and transmits processed signals representing the sensed image (via a communication link 130) to the camera controller 102 for display to a user on the display 104. By manipulating the camera remote-control 108, the user may cause signals to be transmitted (via the camera controller 102 and the communication link 130) to the actuator(s) 118 to cause the actuator(s) 118 to adjust a physical position of the camera head 122, thereby controlling the image displayed on the display 104.

In the FIG. 1 example, the camera 106 is coupled to the camera controller 102 via the communication link 130 so that the camera 106 may be disposed remotely from the camera controller 102 and the camera remote-control 108. The communication link 130 may be implemented in any of numerous ways, and the invention is not limited to the use of any particular type of communication link. For example, the communication link 130 may be implemented using a standard multi-conductor cable, a single cable on which multiple signals are multiplexed, or a wireless communication link (e.g., a radio-frequency (RF) or infrared (IR) communication link). Also, the communication link 130 can be virtually any length, and the invention is not limited to the use of a communication link of any particular length. For example, the communication link 130 may be relatively short (requiring the camera controller 102 to be located in the same room as the camera 106), or may traverse longer distances, e.g., from room-to-room, building-to-building, state-to-state, or country-to-country.

As shown in FIG. 1, the camera controller 102 may comprise a programmed computer (including a processor 110, one or more user-input devices 112, a memory 114, a printer 116, and the display 104). The memory 114 may store a computer program (e.g., software or firmware) which, when executed by the processor 110, cause the processor 110 to perform the various functions described herein. It should be appreciated, however, that the camera controller 102 may be configured in any of numerous ways, and that the invention is not limited to the use of a programmed computer such as that shown in FIG. 1. In alternative embodiments, for example, the camera controller 102 may also comprise dedicated hardware, alone or in combination with a programmed processor. It should also be understood that, in some embodiments, the image generated by the image sensor 124 can be displayed on devices that are driven by circuits other than the processor 102, such that the invention is not limited to the use of a processor-driven display such as that shown in FIG. 1. For example, the display 104 may alternatively be coupled directly to the signal conditioning circuit 120 to display an image based on the signal therefrom.

Additionally, in some embodiments, the camera remote control 108 can be coupleddirectly to the actuator(s) 118 without passing through the processor 110, e.g., when signals from the camera remote-control 108 are not required to be converted/translated before being passed to the actuator(s) 118. In embodiments wherein the display 104 and the camera remote-control 108 do not pass through a common processor, a simple interface unit (not shown) may be used to provide a common connection point for the display 104, the camera remote control 108, and the camera 106 so that only a single cable or other transmission medium is needed to couple the camera 106 to the other components (via such an interface unit), thereby eliminating the cable clutter that would result if a separate cable were used to connect each of the display 104 and the camera remote control 108 to the camera 106.

The display 104 may be a general-purpose video display, a television display, a liquidcrystal display (LCD), or any other device suitable for displaying an image generated by the camera 106. In some embodiments, the memory 114 (e.g., a random access memory (RAM), disk drive, tape drive, writeable compact disk (CD) drive, etc.) of the camera controller 102 can be used to digitally store one or more images generated by the camera 106. Alternatively, an analog storage device, e.g., a video camera recorder (VCR) (not shown), may be used to store a video signal generated by the camera 106. In either case, the stored image may later be displayed on the display 104, or may be displayed and/or stored at a remote location either by transmitting (e.g., over a network such as the Internet, or via a point-to-point communication link) the stored image to the remote location, or by transporting the storage medium (e.g., a CD, diskette, magnetic tape, VCR tape, etc.) on which the image is stored to the remote location.

The camera remote-control 108 may be configured in any of numerous ways, and the invention is not limited to any particular type of remote-control device. In one illustrative embodiment, for example, the camera remote-control 108 is a foot pedal control assembly 1202 (see FIG. 12) including a group of foot-activated switches with which the user may control the camera head 122. This and other implementations of the camera remote-control 108 are described below in connection with FIGS. 12–16.

With respect to the camera 106, the actuator(s) 118 which cause the camera head 122 to move physically may be any device(s) that are capable of performing this function. In one illustrative embodiment, for example, the actuator(s) 118 include a pair of step motors which, in response to electrical signals from the camera controller 102, cause the elevation or azimuth of the camera head 122 to be adjusted, depending on which motor is activated. It should be appreciated, however, that the invention is not limited in this respect, and that actuators other than step motors (e.g., solenoid actuators) may alternatively be used.

As shown in FIG. 1, the actuator(s) 118 may be physically linked to the camera head 122 via one or more mechanical links 132 so that physical forces generated by the actuator(s) 118 can be transferred to the camera head 122 via these links. In such an embodiment, the use of one or more elongated structures as the mechanical link(s) 132 permits the camera head 122 to be disposed remotely from the actuator(s) 118 by a distance equal to the length of the mechanical link(s) 132. In one illustrative embodiment, the mechanical link(s) 132 are configured such that the actuator(s) 118 and the camera head 122 are located, respectively, at proximal and distal ends of the camera 106. In such an embodiment, the distal end of the camera 106 can be made quite small since it need not accommodate the actuator(s) 118 as well as the camera head 122.

As mentioned above, in the illustrative embodiment of FIG. 1, the camera head 122 is coupled to the signal conditioning circuit 120 via the connection 134 so that electrical signals can be transmitted from the camera head 122 to the signal conditioning circuit 120. The use of the connection 134 in this manner permits the camera head 122 to be disposed remotely from the signal conditioning circuit 120 by a distance equal to the length of the connection 134. In one illustrative embodiment, the camera head 122 is disposed near a distal end of the camera 106, and the signal conditioning circuit is disposed proximal of the camera's distal end. Such an embodiment further enables, the camera's distal end to be quite small, since it need not accommodate the signal conditioning circuit 120 along with the camera head 122.

In one illustrative embodiment, the signal conditioning circuit 120 comprises an digital-to-analog converter (DAC) and an amplifier. In such an embodiment, the DAC can convert a digital signal generated by the image sensor 124 into an analog signal, and the amplifier can amplify this analog signal prior to transmitting it to the camera controller 102 or other circuitry. In another embodiment, the signal conditioning circuit 120 comprises only an amplifier which amplifies an analog signal generated by the image sensor 124 prior to transmitting it to the camera controller 102. In either case, the use of an amplifier within the signal conditioning circuit 120 permits a relatively low amplitude signal within the camera 106 to be amplified to a level sufficient for the processor 110 to digitize with adequate resolution, and/or permits the signal from the camera 106 to be transmitted over long cable runs or otherwise transmitted over a relatively long distance to the camera controller 102. It should be appreciated, however, that the invention is not limited in this respect, and that the signal-conditioning circuit 120 may be any of numerous alternative types of signal-conditioning circuits. In alternative embodiments, for example, the signal-conditioning circuit 120 may comprise one or more filters, analog-to-digital converters (ADCs), digital signal processors (DSPs), etc. In fact, in some embodiments, the camera 106 need not include any type of signal-conditioning circuit 120, and the signal from the image sensor 124 may simply be provided directly to the camera controller 102.

The components of the camera head 122 (i.e., the image sensor 124 and the lens assembly 128) may be any of numerous devices suitable for generating electrical signals representing an image sensed by the camera head 122. The image sensor 124 may, for example, include a charge-coupled device (CCD), a metal-oxide semiconductor (MOS) sensor, or a microbolometer (i.e., an infra-red detection array which is capable of perceiving objects at very low levels of light). Alternatively, the image sensor 124 may include a bundle of fiber optic cables which channel light from an image to a remotely-located device that converts the light from the cables into electronic signals representing the image. One example of a lens assembly that may be employed in the camera head 122 is described below in connection with FIGS. 11 and 12.

As mentioned above, in the illustrative embodiment of FIG. 1, the image sensor 124 is coupled to the signal-conditioning circuit 120 via the connection 134. According to one aspect of the present invention, the signal-conditioning circuit 120, the connection 134, and the camera head 122 all are included in a single module (i.e., a camera module) that can be removed from the camera 106 as a unit so that the entire camera module can be removed and replaced with a new camera module when any one of its component parts fails. The failed camera module may then be repaired while enabling the rest of the camera 106 to be used with the replacement module. An example of a camera module 902 (including a signal conditioning circuit 120 (e.g., an amplifier), a connection 134 (e.g., a flexible cable), and a camera head 122) is described below in connection with FIGS. 8 and 9. The use of such a camera module 902 can be advantageous, for example, because it is often difficult to determine which of the module's component parts have failed, thereby making it quicker and easier to replace the entire module without having to identify the precise point of failure.

Similarly, in another embodiment of the invention, all of the actuator(s) 118 are grouped together in a single module (i.e., an actuator module) that can be removed from the camera 106 as a unit so that the entire actuator module can be removed and replaced with a new actuator module when any one of its component parts fails. An example of an actuator module 402 is described below in connection with FIGS. 4 and 5. Upon the failure of any one of the actuator(s) 118, the entire actuator module may simply be replaced, without having to determine which of the actuator(s) 118 has failed, and without having to separate the failed actuator 118 and gears associated therewith from the working actuator 118.

The embodiment of the camera 106 described below includes both the camera module 902 and the actuator module 402. While the use of both of these modules can provide significant advantages, it should be appreciated that the present invention is not limited in this respect, as the modules can also be used separately. Furthermore, some embodiments of the invention do not employ any such modules.

Figure 2:
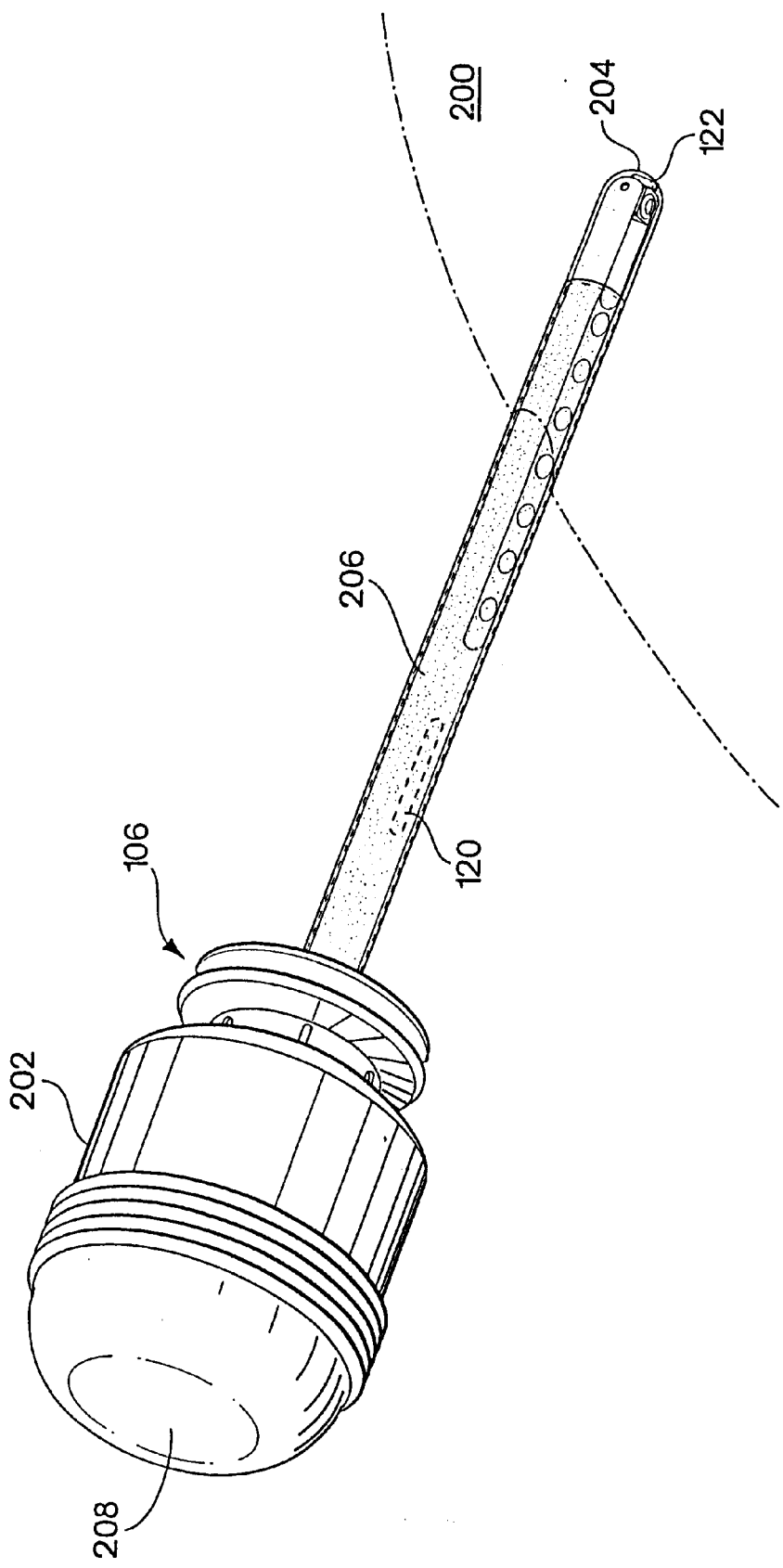
FIG. 2 shows an example of a camera, which may be used in the imaging system of FIG. 1, in accordance with another embodiment of the invention.

One illustrative embodiment of the camera 106 is shown in FIG. 2. As shown, in the FIG. 2 embodiment, the camera 106 is in the form of an elongated scope, which is useful for endoscopic applications or other environments where access is desired to a remote viewing area through a narrow opening. However, it should be appreciated that the invention is not limited in this respect, and that the camera 106 may be configured for use in any of numerous alternative applications.

The illustrative embodiment of FIG. 2 may be used, for example, in endoscopic applications by inserting a distal end 204 of the camera 106 through an incision in a torso 200 of a human body so that the internal portion of the torso 200 can be viewed by the camera head 122. In alternative embodiments, the camera 106 may instead be used to view the internal portions of any other type of cavity, e.g., a cargo hold, a pipe line, a room under surveillance, etc. In the embodiment shown in FIG. 2, the camera head 122 is located adjacent the distal end 204 of the camera 106, the actuator(s) 118 are located inside an upper housing 202 at a proximal end 208 of the camera 106, and the signal-conditioning circuit 120 is located in a section 206 therebetween. In the FIG. 2 embodiment, the significant physical separation of the camera head 122 from both the signal conditioning circuit 120 and the actuator(s) 118 is enabled by the use of an elongated cable as the connection 134 (FIG. 1), and by the use of elongated structures as the mechanical links 132 (FIG. 1). That is, the use of an elongated cable as the connection 134 permits the signal conditioning circuit 120 to be separated from the camera head 122, and the use of elongated structures as the mechanical links 132 permits the actuator(s) 118 (in the upper housing 202) to be separated from the camera head 122.

In the illustrative embodiment of FIG. 2, the physical separation between the camera head 122 and the other components of the camera 106 permits the distal end 204 to be only wide enough to accommodate the camera head 122, without also having to accommodate the actuator(s) 118. In this manner, the distal end 202 may be made very narrow so that the camera 106 can enter the torso 200 (or other cavity) through a very small opening. Alternatively, because of the separation between the camera head 122 and the other components of the camera 106 (e.g., the signal conditioning circuit 120 and the actuator(s) 118), a larger camera head 122 can be used in the distal end 204 of the camera 106 without increasing the width of the distal end 204. The use of a larger camera head may, for example, permit larger optical elements (e.g., the lens assembly 128 and the image sensor 124) to be used, thereby increasing image resolution.

Figure 3:
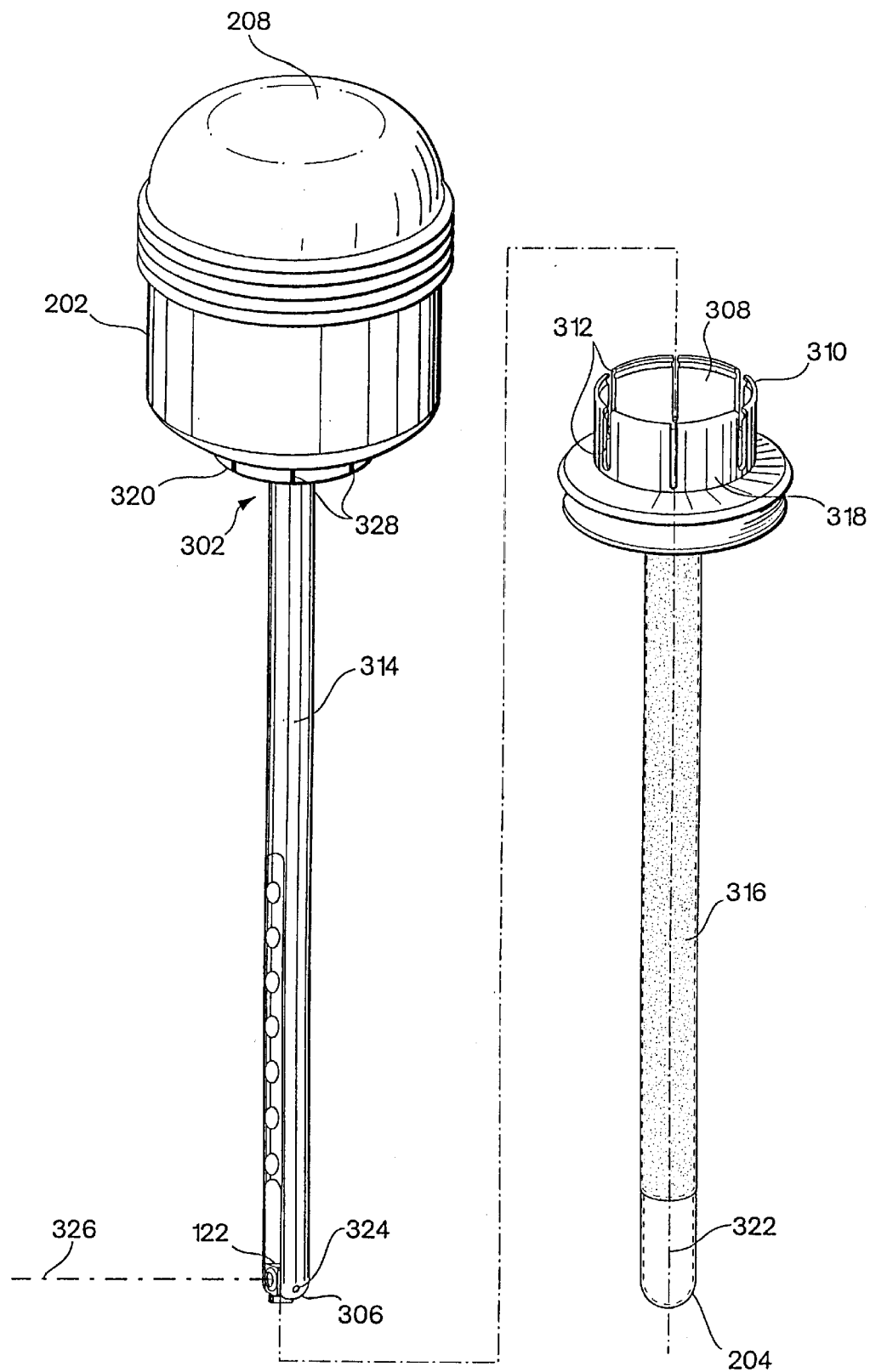
FIG. 3 is an exploded view of the camera of FIG. 2.

As shown in FIG. 3, the camera 106 may include an elongated sheath 316, and an elongated support member 314 (to which the camera head 122 is attached) disposed within the sheath 316. As shown, the camera 106 may be assembled by inserting a distal end 306 of the support member 314 into an opening 308 at a proximal end 310 of the sheath 316. The distal end 306 is inserted into the sheath 316 until the proximal end 310 of the sheath 316 abuts an annular section 320 at a distal end 302.of the upper housing 202. When the proximal end 310 contacts the annular section 320, gaps 312 between fingers 318 at the proximal end 310 permit the fingers 318 to separate outwardly so as to accommodate the annular section 320.

In the illustrative embodiment of FIG. 3, tabs 328 are provided on the annular section 320 that are sized and positioned so as to fit within the gaps 312 when the sheath 316 is attached to the upper housing 202. This mating of the tabs 328 with the gaps 312 inhibits the sheath 316 from rotating with respect to the upper housing 202 when attached thereto. Alternatively, one or more other portions of the sheath (e.g., one or more of the fingers 318) may be tabbed, and one or more corresponding portions of the upper housing 202 (e.g., one or more sections of the annular section 320) may be slotted, or vice versa, so that the mating of the "tabs" with the "slots" inhibits the sheath 316 from rotating or otherwise moving with respect to the upper housing 202 once these components are locked into engagement.

In one embodiment, the sheath 316 is rigid so that, when the support member 314 is accommodated by the sheath 316, the support member 314 is permitted to rotate within the sheath 316, and the sheath 316 remains spaced from the support member 314 throughout the support member's permitted range of rotation. Because the camera head 122 is attached to the support member 314, rotation of the support member within the sheath 316 also causes the camera head 122 to rotate within the sheath 316 so that the azimuth of the camera head 122 can be adjusted while the sheath remains stationary with respect to the subject being viewed. In the illustrative embodiment of FIG. 3, the elevation of the camera head 122 also can be adjusted within the sheath 316 without moving the sheath 316 with respect to the subject being viewed. As discussed in more detail below, this ability to move the camera head 122 so that the imaging axis 326 is oriented in virtually any direction while keeping the sheath 316 stationary with respect to the subject being viewed provides significant advantages.

In one embodiment for use in medical applications, the sheath 316 is sterile so that, when it is attached to the upper housing 202, it creates a sterile barrier between the elements accommodated by the sheath (e.g., the support member 314 and the camera head 122) and the environment outside the sheath 316 (e.g., the patient's torso 200 of FIG. 2). In such an embodiment, because of this sterile barrier, it is not necessary to sterilize the components accommodated by the sheath 316, which provides significant advantages over prior art imaging systems in which such sterilization is required. For example, because some components need not be sterilized between procedures, these components are immediately available for subsequent procedures, and the physician does not have to wait for the components to be sterilized before re-use. Rather, the physician may immediately begin a new procedure by using a new (or newly-sterilized) sterile sheath 316 in combination with the previously-used, unsterile components. Additionally, because some components of the camera 106 need not be sterilized between uses, the risk that these components will be damaged during the sterilization process is eliminated.

In one embodiment, a flexible, sterile drape (not shown) is attached to the sheath 316 (e.g., over a rim portion 304 of the sheath 316). Such a drape may be extended proximally over the upper housing 202 and a cord (not shown) coupling the camera 106 to the camera controller 102 so that the sheath 316 and the drape together create a sterile barrier between all components of the camera 106 and the subject being viewed.

In one embodiment of the present invention, an optically clear material (e.g., plastic or glass having an "S1" finish), is used to form the sheath to ensure that the sheath does not degrade the quality of the image viewed by the camera. It should be appreciated that, when the sheath 316 is used in a camera such as that shown in FIG. 2, the imaging axis of the camera may pass only through certain portions of the sheath when the camera is in operation. In the embodiment of FIGS. 2–3, for example, when the camera 106 is being used, the imaging axis 326 passes only through a small portion 322 (FIG. 3) of the sheath 316 near the camera's distal end 204. In another embodiment of the invention, optically-clear materials are used only for the portion(s) of the sheath that affect the quality of the image sensed by the camera, and less expensive materials are used for the remaining portions of the sheath. In the illustrative embodiment of FIGS. 2 and 3, for example, only the small portion 322 (e.g., a length of "1.25" inches) of the sheath 316 can be made of an optically-clear material, and the remainder of the sheath 316 can be formed (e.g., as an opaque extrusion) from low-cost plastic, glass and/or other low-cost materials. By producing the sheaths in such a low-cost manner, each sheath 316 may, if desired, be disposed of after a single use. It should be appreciated that, in alternative embodiments, materials other than those mentioned may be used to make the sheath 316, and the invention is not limited to the specific materials identified.

The optically-clear portion 322 of the sheath 316 may be secured to the opaque portion of the sheath 316 in any of numerous ways, and the invention is not limited to any particular securing technique. For example, in one embodiment, the optically-clear portion 322 is secured to the non-optically-clear portion using an epoxy. Alternatively, the optically-clear portion 322 may be secured to the non-optically-clear portion using sonic-welding, press-fitting, or any other technique.

In one embodiment, the curvature of the distal end of the sheath 316 is spherical so that, when the camera head 122 rotates about a pivot point 324 (as described below), the head remains a constant distance from the inner surface of the sheath 316, and an imaging axis 326, along which the camera head 122 senses an image, remains normal to the inner surface of the sheath. In this manner, the angle at which the imaging axis 326 intercepts the inner surface of the sheath 316 does not change as the camera head 122 moves within the sheath 316, and does not cause the image sensed by the camera head 122 to be distorted.

While sheaths having specific characteristics and specific manufacturing techniques for producing such sheaths have been described herein, it should be appreciated that the invention is not limited to the particular sheaths or the particular manufacturing techniques described.

Figure 4:
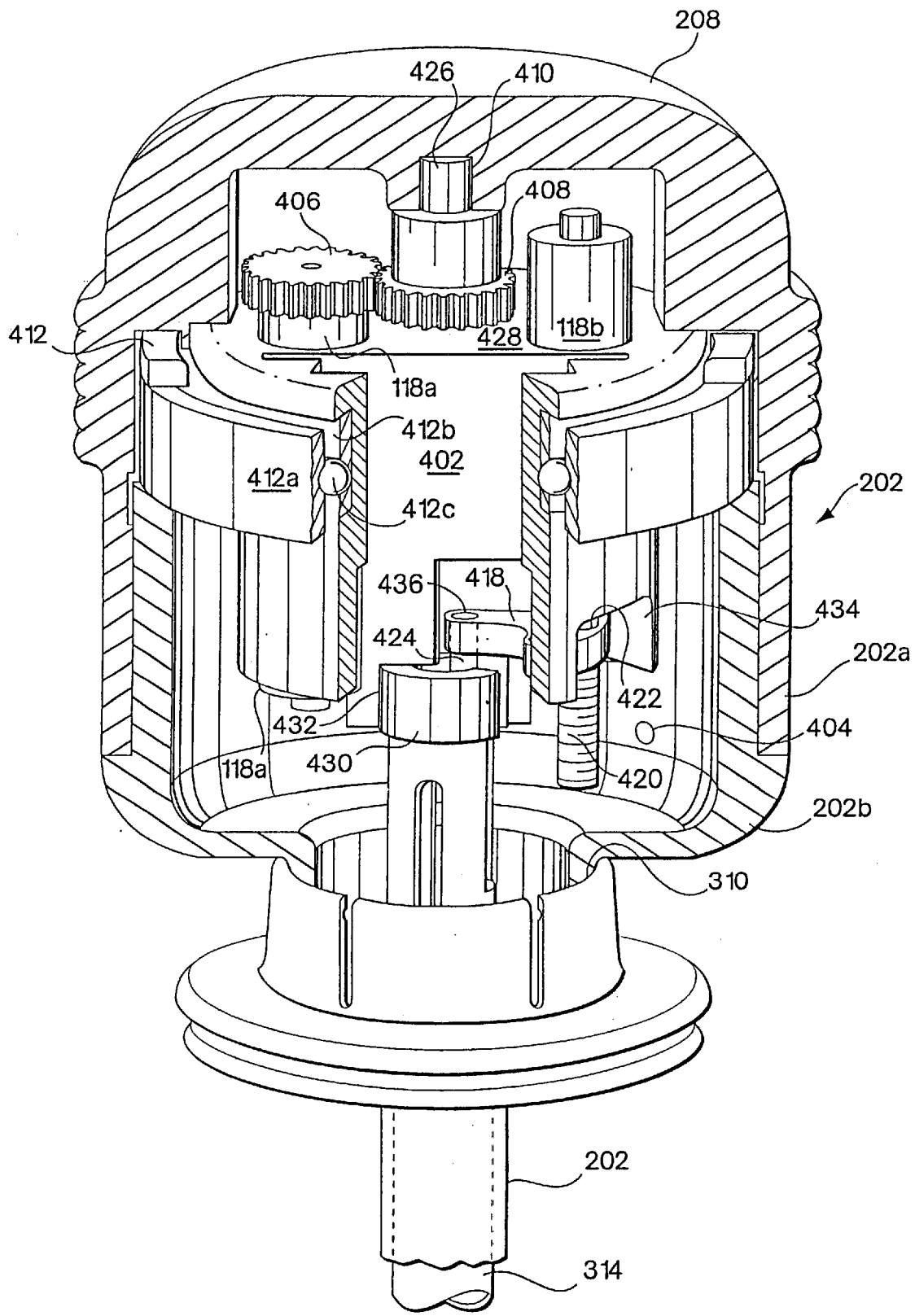
FIG. 4 illustrates an exemplary implementation of an upper housing of the camera of FIGS. 2–3 in accordance with one embodiment of the invention.

FIG. 4 is a perspective, sectional view of the upper housing 202 of FIGS. 2–3 according to one embodiment of the invention. In the illustrative embodiment of FIG. 4, the upper housing 202 includes two separate housing portions 202a and 202b which are mated together. The portions 202a–b may be secured together in any of numerous ways, and the invention is not limited to the use of any particular securing technique. In one embodiment, for example, the sections 202a–b are secured together using an epoxy. Alternatively, the sections 202a–b may be sonic-welded, press-fit, or otherwise secured together.

Figure 5:
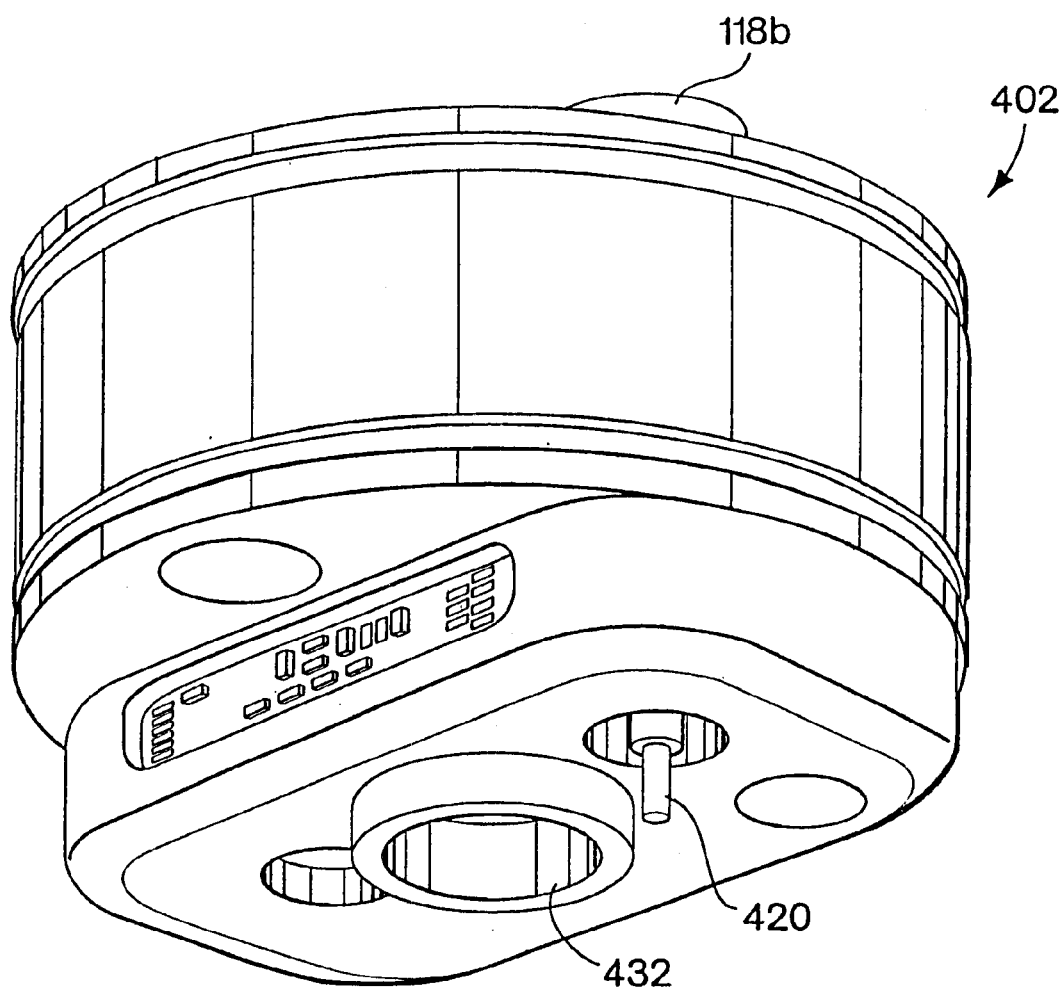
FIG. 5 illustrates an exemplary implementation of an actuator module of the camera of FIGS. 2–3 in accordance with one embodiment of the invention.

As mentioned above, according to one aspect of the invention, each of a pair of actuators (e.g., step motors) is included within a single actuator module that can be inserted in and removed from the upper housing 202 as a unit. The illustrative embodiment of FIG. 4 incorporates this aspect of the invention by the use of an actuator module 402 which includes a pair of step motors 118a–b. FIG. 5 shows the actuator module 402 separated from the upper housing 202.

As discussed above, in one embodiment of the invention, the support member 314 is rotatable within the sheath so that the azimuth of the camera head 122 can be adjusted without moving the sheath 316 with respect to the subject being viewed. Another advantageous feature of the camera 106 (as illustrated best in FIG. 4) is that rotation of the support member 314 can also be accomplished without rotating the upper housing 202 with respect to the subject being viewed. That is, in the illustrative embodiment of FIG. 4, the upper housing 202 and the sheath 316 are held stationary with respect to one another, and the actuator module 402 and the support member 314 (which are held stationary with respect to one another) rotate as a unit within the upper housing 202 and the sheath 316. In this manner, all external portions of the camera 106 remain stationary with respect to the subject being viewed, and only portions internal to the camera 106 move with respect to the subject when the position of the camera head 122 is adjusted.

The rotation of the actuation module within the upper housing 202 may be effected in any of numerous ways, and the invention is not limited to any particular technique for accomplishing this result. In the FIG. 4 embodiment, for example, the actuation module is rotatably mounted within the upper housing using a bearing ring assembly 412 (also shown in FIGS. 6A–B) interposed between the actuator module 402 and an inner surface of the upper housing 202. As shown in the illustrative embodiment of FIGS. 4 and 6, the bearing ring assembly 412 includes an outer ring 412a, an inner ring 412b, and a plurality of ball bearings 412c sandwiched therebetween. In this configuration, the outer ring 412a is permitted to rotate freely about the inner ring 412b.

Figure 6A:
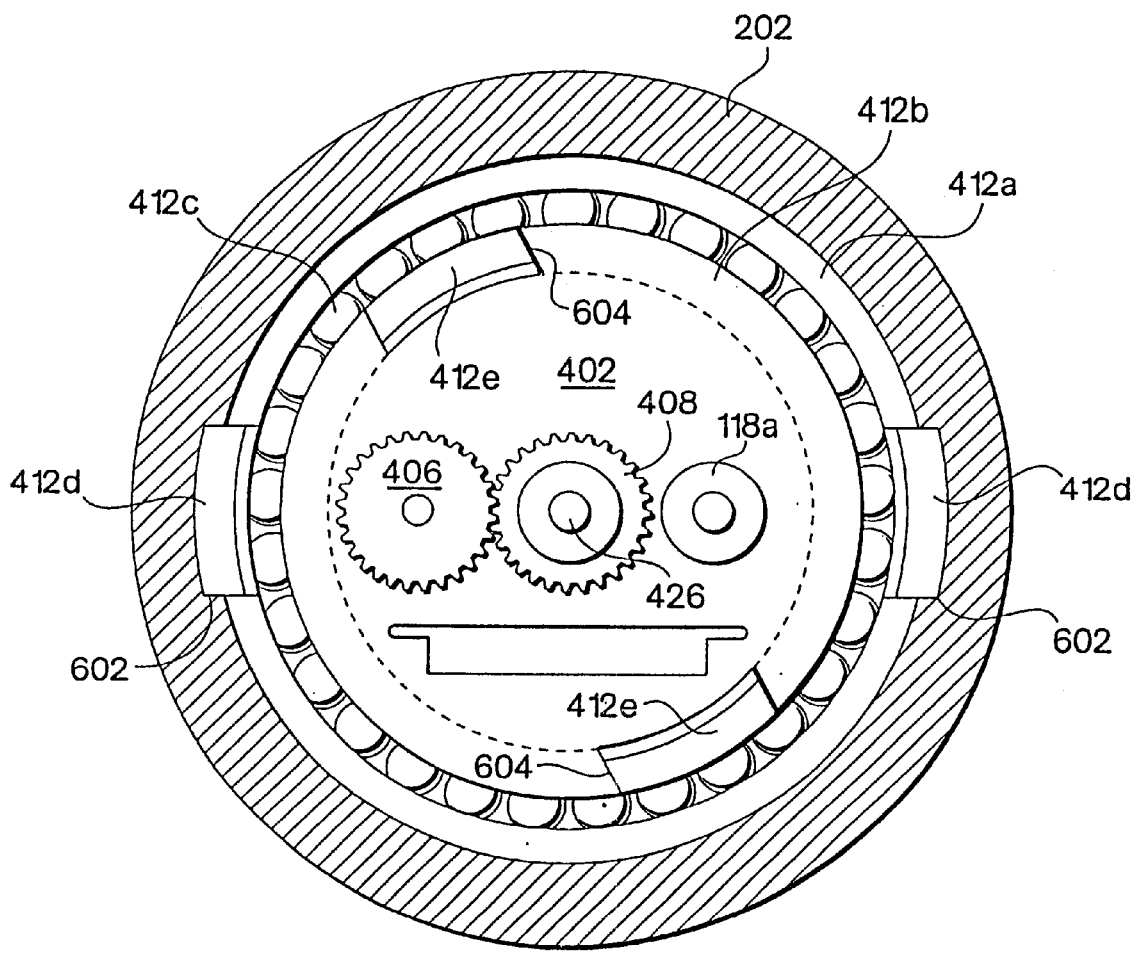
FIGS. 6*a*–*b* illustrates an exemplary implementation of a bearing ring assembly of the camera of FIGS. 2–3 in accordance with one embodiment of the invention.
Figure 6B:
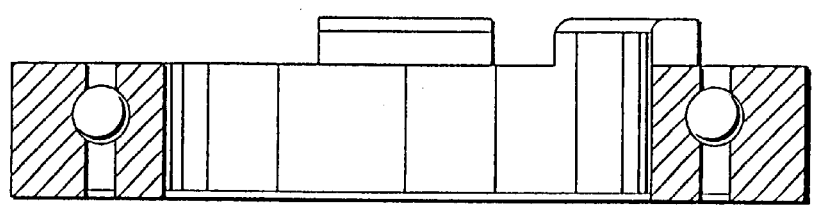

As is illustrated best in FIG. 6A, a pair of locking members 412d of the bearing ring assembly 412 engage corresponding notches 602 in the inner surface of the upper housing 202, thereby preventing the outer ring 412a from moving with respect to the upper housing 202. Similarly, a pair of locking members 412e engage corresponding notches 604 in the actuator module 402 so as to prevent the inner ring 412b from moving with respect to the actuator module 402. Thus, because of the presence of the bearing ring assembly 412, the actuator module 402 is permitted to rotate freely within the upper housing unit 202.

While the bearing ring assembly 412 is described herein as being used for a specific application, i.e., an actuator module that is rotatable within a camera housing, it should be appreciated that the invention is not limited in this respect. Rather, the bearing ring assembly 412 may be used in any application wherein a rotational relationship between two or more components is desired. Although bearing ring assemblies are known, it is believed that the use of one or more mating features such as the locking members 412d and 412e that permit either (or both) of the bearing rings to be held in a fixed physical relationship with another component represent a notable advancement over the state of the art. Therefore, a ring assembly having such features can be used in any numerous other applications wherein bearing rings are employed.

In the illustrative embodiment of FIG. 4, the actuator module 402 has a gear 408 rotatably secured to a top portion 428 thereof so as to permit the gear 408 to rotate with respect to the actuator module 402. An upper extension 426 of the gear 408 is fixably secured within a corresponding cavity 410 in the upper housing 202 so that the gear 408 is not permitted to rotate with respect to the upper housing 202.

One of the motors included in the actuator module 402 of FIGS. 4–6 is an azimuth motor 118a having a gear 406 attached to a drive shaft thereof so that the gear 406 rotates when the azimuth motor 118a is activated. In the illustrative embodiment shown, the gear 406 is mated with the gear 408 so that, when the azimuth motor 118a is activated, the rotation of the gear 406 causes the entire actuator module 402 and the inner ring 412b to rotate with respect to the upper housing 202 and the outer ring 412a.

In the FIG. 4 embodiment, a proximal end 430 of the elongated support member 314 is secured within a corresponding cavity 432 at the distal end of the actuator module 402 so that the elongated support member 314 is held stationary with respect to the actuator module 402. Therefore, when the actuator module 402 is caused to rotate within the upper housing 202, the elongated support member 314 is also caused to rotate with respect to the upper housing 202.

As discussed above, the proximal end 310 of the sheath 316 may be secured to the distal end 302 of the upper housing 202. In one embodiment, the sheath 316 is fixedly secured to the upper housing 202 so that the sheath 316 is held stationary with respect to the upper housing 202. Therefore, when the actuator module 402 is caused to rotate within the upper housing 202, the elongated support member 314 is caused to rotate within the sheath 316.

When the communication link 130 (FIG. 1) between the camera 106 and the camera controller 102 comprises a multi-conductor cord, this cord may pass through a hole 404 (FIG. 4) in the upper housing 202 and may be held therein using a rubber grommet or the like. Individual wires of this cord may be connected to the actuators 118a–b, the signal conditioning circuit 120 and one or more lights (described below in connection with FIG. 8). In one embodiment, the rotation of the actuator module 402 within the upper housing 202 is limited to plus or minus "180" degrees so as to prevent the wires in the upper housing from becoming stretched, broken, or tangled. Alternatively, slip rings may be employed to establish electrical connections so that the actuator module 402 is permitted to rotate within the upper housing 202 without limitation. When the communication link 130 is wireless, a transceiver (not shown) may be provided in the upper housing 202 to permit the camera controller to communicate with the components of the camera 106.

Figure 7:
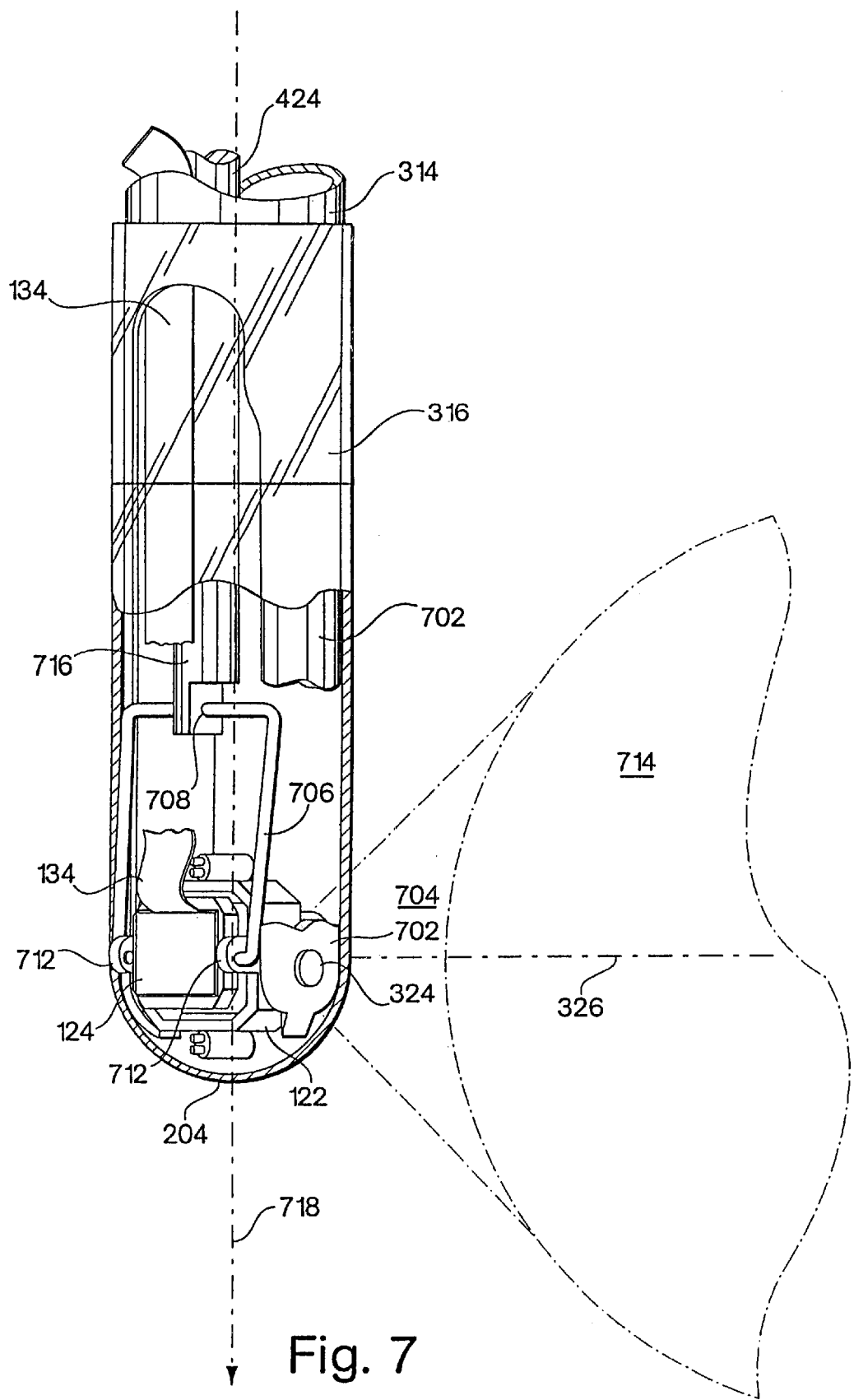
FIG. 7 shows an illustrative embodiment of the distal end of the camera of FIGS. 2–3 wherein the distal end includes components for positioning the viewing elements of the camera.

FIG. 7 illustrates one exemplary implementation of a mechanical assembly that may be employed in the camera 106 to cause the camera head 122 to move to alter a viewing area 704 thereof. Referring to FIG. 7 in conjunction with FIG. 4, it can be seen how activation of the azimuth motor 118a (which causes the elongated support member 314 to rotate within the sheath 316) causes the camera head 122 to rotate within the sheath 316, thereby adjusting an azimuth position the camera head 122 and altering the viewing area 704 thereof. Because rotation of the support member 314 causes the azimuth of the camera head 122 to be adjusted, the support member 314 serves as one of the mechanical links 132 (FIG. 1) which serves to transfer physical forces from the azimuth motor 118a to the camera head 122.

In the illustrative embodiment of FIG. 4, the actuator module 402 also includes an elevation motor 118b. In the FIG. 4 example, a threaded member 420 is coupled to a drive shaft (or is itself the drive shaft) of the elevation motor 118b so that activation of the elevation motor 118b causes the threaded member 420 to rotate. In the FIG. 4 embodiment, the threaded member 420 is threaded within a corresponding threaded hold 422 in an arm 418. The end of the arm 418 that includes the hole 422 is contained within a cavity 434 located in the distal portion of the actuator module 402 such that the arm 418 is permitted to move distally and proximally (i.e., up and down) within the cavity 434, but is not permitted to move sideways within the cavity 434. Therefore, activation of the elevation motor 118b causes the threaded member 420 to rotate within the threaded hole 422, causing the arm 418 to move distally and proximally with respect to the actuator module 402. In the FIG. 4 embodiment, a proximal end of an actuation rod 424 is inserted through a second hole 436 in the arm 418, and is fixedly secured therein so that the actuation rod 424 is held stationary with respect to the arm 418. Thus, in the illustrative embodiment shown, movement of the arm 418 distally and proximally causes the actuation rod 424 to move distally and proximally within the sheath 316.

In the illustrative embodiment of FIG. 7, a distal end 716 of the actuation rod 424 has a hole 708 therein through which an upper portion of a bail 706 is inserted so that the bail 706 is permitted to rotate within the hole 708. As illustrated in FIG. 7, a lower portion of the bail 706 may be movably connected to a pair of arms 712 extending from a rear portion of the camera head 122. In the FIG. 7 embodiment, at least one arm 702 (partially cut away in FIG. 7) of the elongated support member 314 is pivotally connected to a pivot point 324 on a side of the camera head 122 so that the camera head 122 is permitted to pivot about the pivot point 324. Therefore, the distal and proximal movement of the actuation rod 424 (in response to the elevation motor 118b being activated) causes the elevation of the camera head 122 and the viewing area 704 thereof to be adjusted. Because movement of the actuation rod 424 causes the elevation of the camera head 122 to be adjusted, the actuation rod 424 serves as another of the mechanical links 132 (FIG. 1) which serves to transfer physical forces from the azimuth motor 118b to the camera head 122.

The range of elevations through which the camera head 122 can be oriented, by pivoting about pivot point 324 (FIG. 7), may vary depending on the physical configuration of the camera 106 and the application for which the camera 106 is being used. In the embodiment of FIGS. 2–7, for example, in which the camera 106 is designed for use in an endoscopic surgical procedure, the camera head 122 pivots through an angle of approximately "175" degrees about the pivot point 324. The camera can be considered as including a reference axis 718 that extends along a longitudinal axis of the support member 314. In one embodiment of the invention, the camera 122 can be pivoted to form any angle between the imaging axis 326 (FIG. 3) and the reference axis 718 up to a maximum of "165" degrees. The elevation limit of "165" degrees from the reference axis 718 defines the elevation angle at which the viewing area 704 begins to encompass the camera 106 itself, rather than the subject matter to be viewed. In addition, to ensure that the support shaft need not be repeatedly rotated when viewing an area substantially in-line with the reference axis 718, in one embodiment of the invention the camera 122 can also be pivoted in the opposite direction to form any angle between the imaging axis 326 (FIG. 3) and the reference axis 718 up to a maximum of "10" degrees.

It should be appreciated that, although a particular range of pivoting of the camera head 122 has been described in connection with the embodiment of FIGS. 2–7, the invention is not limited in this respect. In alternative embodiments, the camera 106 can be configured such that the camera head 122 can be oriented throughout a wider or narrower range of elevations than that described. Preferably, the camera 106 is configured such that the imaging axis 326 of the camera head 122 is capable of being elevated to an angle of at least "45" degrees from the reference axis 718, more preferably to an angle of at least "90" degrees, and even more preferably to an angle of at least "135" degrees.

In operation, when the distal end 204 of the camera 106 is inserted, for example, into a body of a patient, a user who is viewing an object 714 (located in the viewing area 704) on the display 104 (FIG. 1) is able to use the camera remote-control 108: (1) to activate the azimuth motor 118a to adjust the azimuth of the camera head 122, and (2) to activate the elevation motor 118b to adjust the elevation of the camera head 122. The user therefore is permitted to view virtually any position within the area of interest in the patient's body, without requiring the sheath to be moved or rotated within the patient's body. This ability to adjust the viewing area 704 without moving the sheath 316 within the patient's body can be particularly advantageous because friction between the sheath and the patient's body can cause tissue damage and/or irritation.

With respect to the above-described actuators and mechanical links used to adjust the elevation and azimuth of the camera head 122, it should be understood that these are only examples of mechanisms that can be used to cause the camera head 122 to move within the sheath 316, and that the invention is not limited to the use of the particular camera-position control mechanisms described. Other types of actuators and/or mechanical links that perform similar functions may alternatively be employed. Also, it should be understood that the invention is not limited to embodiments in which one actuator controls the azimuth of the camera head 122 and another actuator controls its elevation. In alternative embodiments, for example, one actuator may cause the camera head 122 to pivot about a first pivot axis in a first plane, and another actuator may cause the first plane to pivot about a second pivot axis that is transverse to the first pivot axis. It should further be appreciated that multiple actuators need not be employed in all embodiments, and that the camera head 122 may alternatively be caused to move in only a single plane, or may otherwise have a lesser range of motion than that described above.

Figure 8:
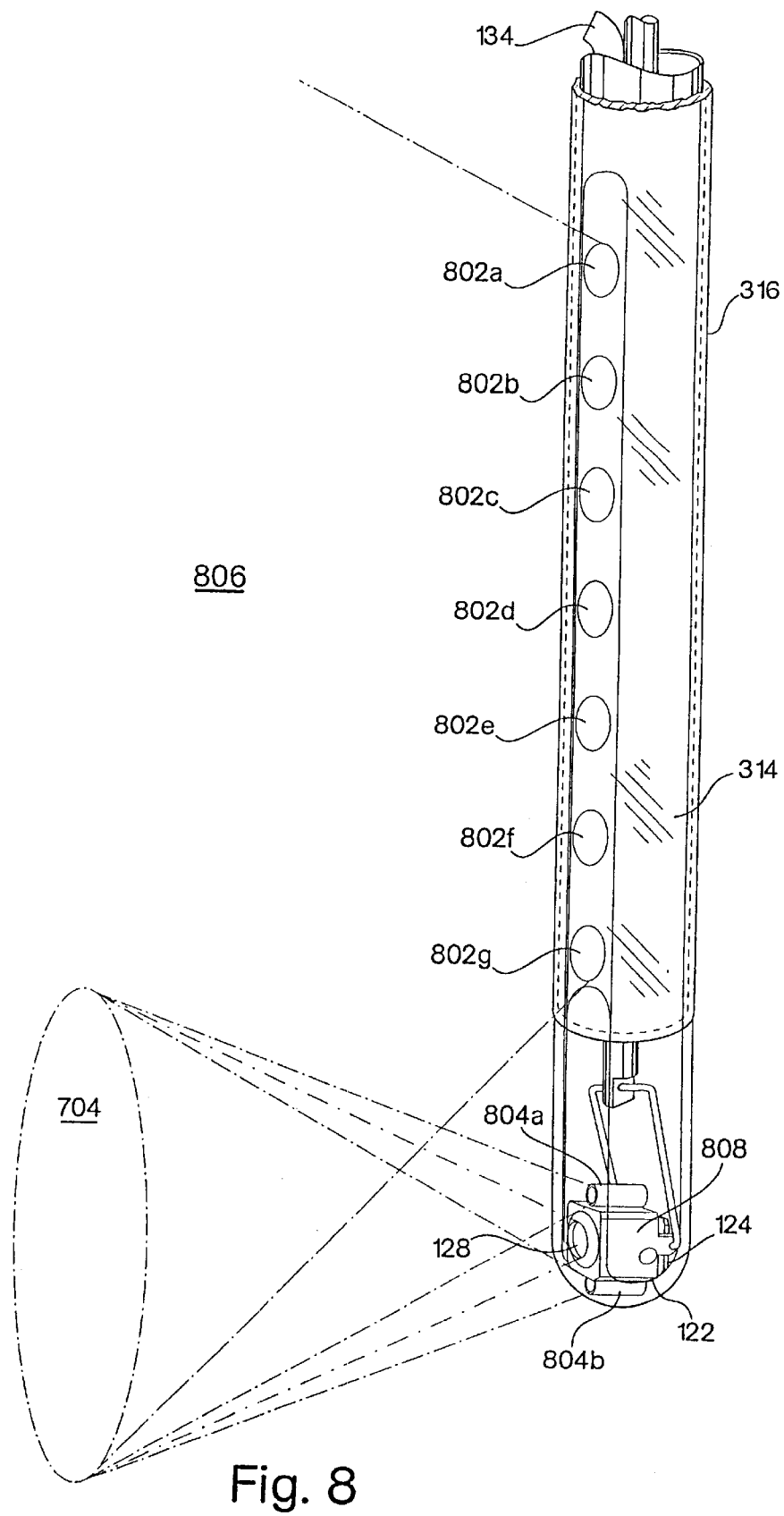
FIG. 8 illustrates an exemplary lighting system that may be used to illuminate a viewing area of the camera of FIGS. 2–3 in accordance with one embodiment of the invention.

In one embodiment of the invention, the camera 106 includes an on-board lighting scheme that permits the camera 106 to be used in poorly illuminated areas, e.g., inside a patient's body, without requiring a separate light source to be provided to illuminate the area being viewed. FIG. 8 illustrates an example of such a lighting scheme. In the illustrative embodiment of FIG. 8, a set of seven diffused lights 802a–g are powered via the connection 134, and are disposed on one side of the elongated support shaft 314 so that a relatively wide area 806 on that side of the support shaft is illuminated. It should be understood, however, that in alternative embodiments, additional or fewer diffused lights may be used, and the diffused lights may be arranged in configurations (e.g., on both sides of the support shaft 314) other than that shown in FIG. 8.

In the FIG. 8 embodiment, in addition to the diffused lights 802a–g, a pair of focused lights 804a–b are disposed on either side of the camera head 122 so that the viewing area 704 is particularly well illuminated by these focused lights 804a–b. As shown, the lights 804a–b may be secured to the camera head 122 so as to move with the camera head 122 and be illuminating the viewing area 704 at all times. As with the diffused lights 802, it should be appreciated that the invention is not limited in this respect, and that, in alternative embodiments, additional or fewer focused lights may be used, and the focused lights may be arranged in any of a number of alternative configurations. Also, it should be appreciated that some embodiments may include only diffused lights, or only focused lights, and that the invention is not limited to embodiments that employ both.

When the camera 106 is moved to a location that is at a lower temperature than the environment from which the camera 106 was moved, the temperature difference may cause the atmosphere inside the sheath 316 to cool, thereby causing condensation to form on an inner surface of the sheath 316. Such a phenomenon can occur, for example, when the camera 106 is inserted into a cavity of a patient's body that has been insufflated with air, carbon dioxide, or other gas(es), because the flow of gas into the cavity tends to cause the cavity to become colder than both the atmosphere outside the patient's body and the patient's normal body temperature.

In one embodiment, one or more of the lights 802a–g and 804a–b can be selected to produce a sufficient amount of heat to inhibit moisture from condensing on the inner surface of the sheath 316 when the camera 106 is inserted into a cavity that is colder than the environment in which the camera was previously located. For example, in embodiments of the invention for use in surgical applications, one or more of the lights 802a–g and 804a–b may be selected and/or controlled to produce enough heat to prevent any moisture from condensing on the surface of the sheath 316 when the system is inserted in a patient's body by maintaining the temperature within the sheath above a normal body temperature (e.g., "37" degrees Celsius). In one embodiment, in order to comply with current guidelines of the United States Food and Drug Administration, the heat generated by the focused lights 804a–b maintains the temperature within the sheath: (a) above "37" degrees Celsius throughout the sheath, (b) below "45" degrees Celsius near the camera's distal end 204, and (c) below "41" degrees Celsius near the proximal end 310 of the sheath 316. It should be appreciated, however, that the amount of heat generated may be adjusted to comply with different guidelines, or may be adjusted for use in environments other than a patient's body.

Figure 9:
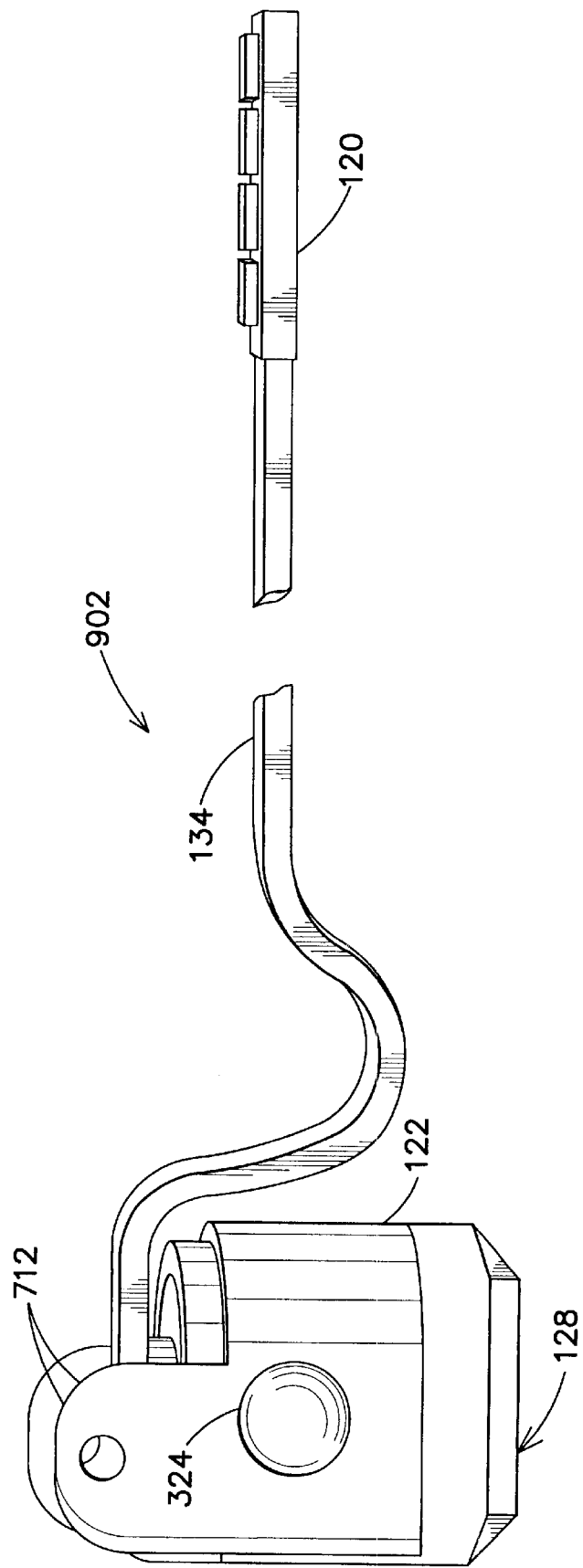
FIG. 9 shows an illustrative implementation of a camera module of the camera of FIGS. 2–3 in accordance with one embodiment of the invention.

In the illustrative embodiment of the invention shown in FIGS. 7–9, the connection 134 between the signal-conditioning circuit 120 and the camera head 122 is formed using a multi-conductor flexible cable. Signals from the image sensor 124 (e.g., a CCD), as well as power signals for the diffused lights 802a–g and the focused lights 804a–b, may be fed through this flexible cable. As shown in FIG. 7, the image sensor 124 may comprise a CCD to which the flexible cable is connected. In embodiments of the invention that employ a flexible cable as the connection 134, the optical elements in the camera head 122 that focus and receive light from an image being sensed (e.g., the lens assembly 128 and the image sensor 124) need not be in-line with the signal conditioning circuit 120 or other elements of the camera 106, and can be positioned independently therefrom. This is in contrast to a conventional camera in which the lens, the viewing aperture and the recording medium (e.g., film) are optically aligned within the body of the camera. Because the camera head 122 can be positioned independently from the other elements of the camera 106, the camera head 122 can be rotated within the distal end of the sheath 316 without also rotating the other camera elements therein. This feature enables the distal end 204 of the camera 106 to be smaller than if all of the components of the camera 106 were required to rotate in unison within the sheath 316. Although using a flexible circuit as the connection 134 provides numerous advantages, it should be appreciated that the invention is not limited in this respect, and that the connection 134 may be formed using a number of alternative types of connectors.

As mentioned above, according to one aspect of the invention, the signal-conditioning circuit 120, the connection 134, and the camera head 122 of the camera 106 (FIG. 1) all are included within a single camera module which may be inserted in and removed from the camera 106 as a unit. The embodiment of FIGS. 7–9 incorporates this aspect of the invention by employing a camera module 902 (see FIG. 9) which includes the amplifier circuit 120 (not shown in FIG. 8), the flexible cable 134, and the camera head 122. FIG. 9 shows an example of how the camera module 902 may appear when separated from the other components of the camera 106. Although not illustrated in FIG. 9, in some embodiments, the diffused lights 802a–g and/or the focused lights 804a–b may also be included in the camera module 902. In embodiments of the invention that employ the camera module 902 of FIGS. 7–9, when any one of the constituent components of the camera module 902 fails, the entire camera module 902 may be swapped for a new camera module so that the camera 106 may still be used while the swapped-out camera module is being repaired.

Figure 10:
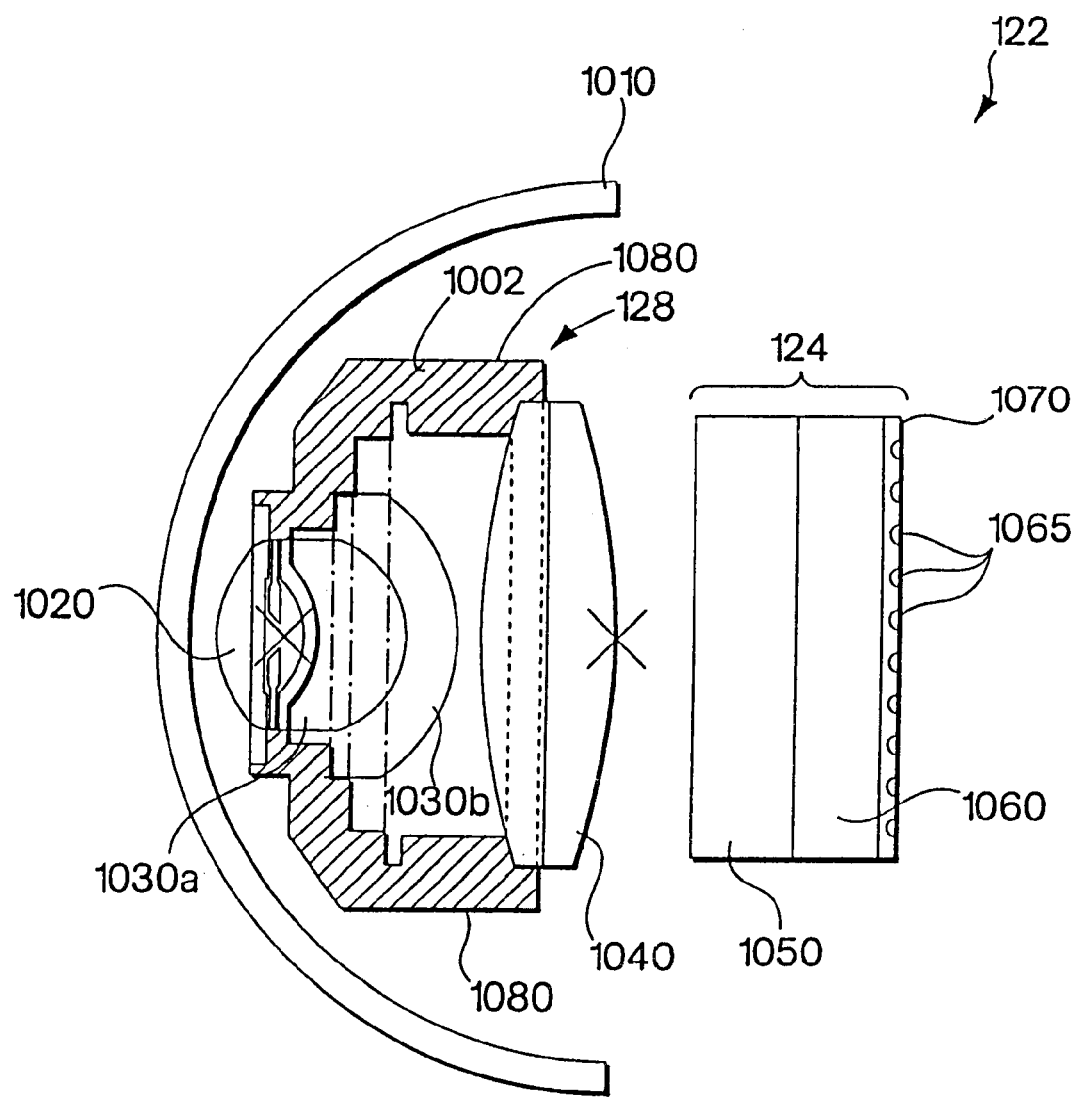
FIGS. 10–11 shows an illustrative implementation of a lens assembly of the camera of FIGS. 2–3 in accordance with one embodiment of the invention.

The lens assembly 128 (FIG. 1) may be configured in any of a number of ways, and the invention is not limited to any particular configuration. In one embodiment, the lens assembly 128 acts as a constant focus lens and does not require any focusing or positioning mechanism. Because focusing a lens typically requires components of the lens assembly to be moved over a certain distance, and requires a focusing mechanism which consumes space, the use of a constant focus lens enables the distal end of a camera (such as the endoscopic camera 106) employing this type of lens assembly to be made smaller than a focused lens assembly. FIG. 10 shows an illustrative example of a constant focus lens assembly.

Figure 11:
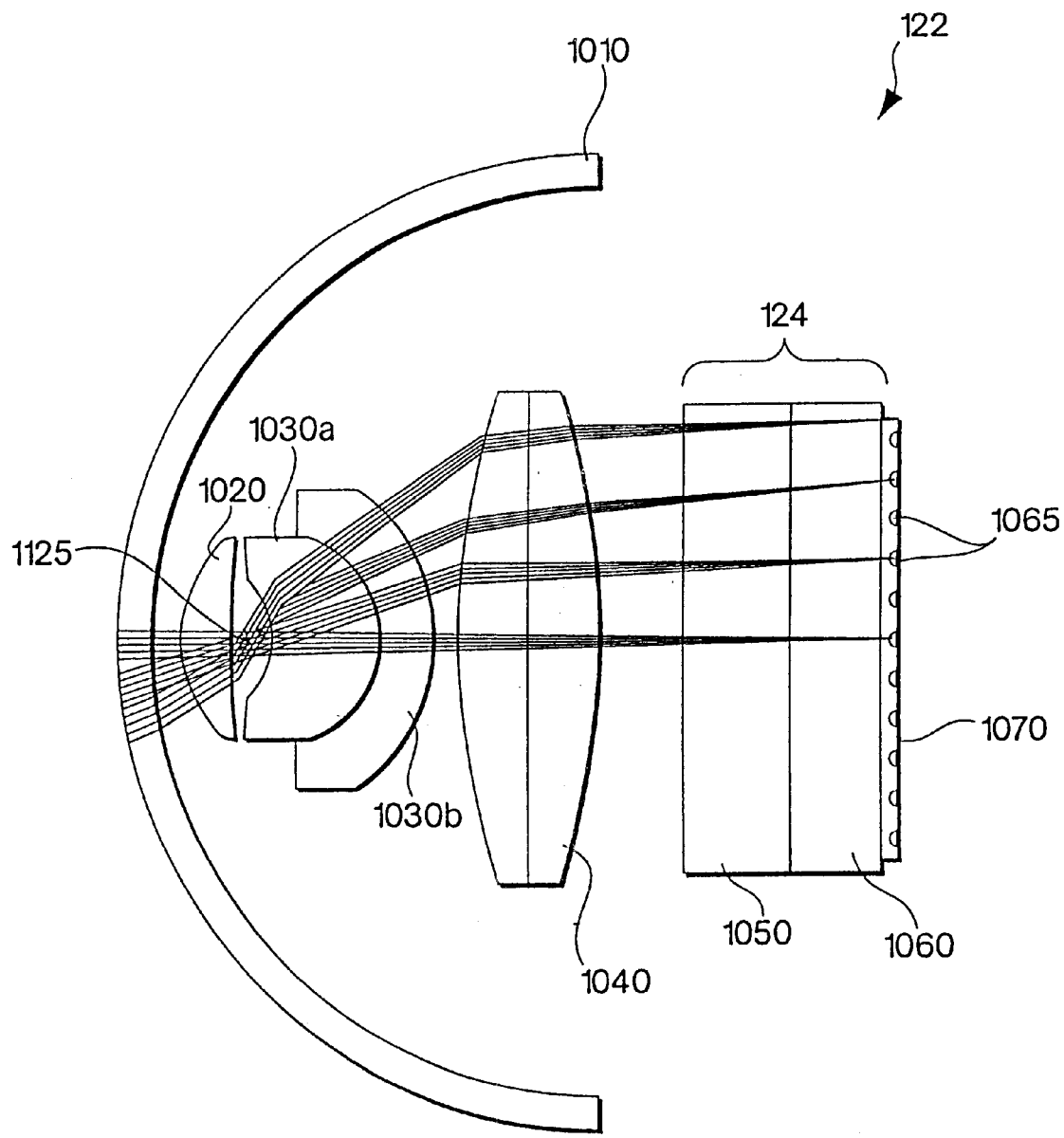

In the FIG. 10 example, the lens assembly 128 may be employed to focus an image onto the image sensor 124 (e.g., a CCD) within the camera head 122. An example of how the lens assembly 128 may be positioned with respect to the other components in the camera 106 is shown in FIG. 8. As shown in FIG. 10, the lens assembly 128 may include a lens housing 1002, and several lenses 1020, 1030, 1040 supported thereby. FIG. 11 illustrates how the lenses 1020, 1030, 1040 may be used to focus light onto the image sensor 124.

In one embodiment, an outer surface 1080 of the lens housing 1002 is threaded so that the lens housing 1002 may be screwed into position within a correspondingly threaded cavity (not shown) within a camera housing 808 (FIG. 8) that also supports the image sensor 124. In this manner, the distance between the lens assembly 128 and the image sensor 124 may be optimized by rotating the threaded lens housing 1002. Once this distance is optimized, the lens housing 1002 may be secured within the camera housing 808, for example, using an epoxy adhesive. In one embodiment, an adhesive that forms a bond that can be readily broken when heated or otherwise subjected to an abnormal environmental condition may be used so that the lens assembly 128 can be readily replaced if defective.

The lens assembly 128 provides a constant focus lens array which can be used to focus light from a target onto an the image sensor 124. Optically, one embodiment of the lens assembly 128 has an effective focal length of "3.53" mm in air, an F number of "11.2," and an angle of view of "34" degrees. These optical characteristics permit high resolution images to be taken of any object that is more than approximately one inch away from the lens assembly 128 without requiring the use of focusing or lens positioning equipment. Because the lens assembly 128 does not require any sort of lens positioning equipment to focus light on the CCD, the lens assembly 128 can be quite small (e.g., in one embodiment, the lens assembly 128 is less than "5" mm in diameter and less than "5" mm in depth). This permits the lens assembly 128 to be used in a variety of different devices. For example, the small size of the lens assembly 128 is advantageous for use in the camera 106 of FIGS. 2–9 used in minimally-invasive surgical/diagnostic procedures.

The lens assembly 128 may also be advantageously used in any of numerous other applications, e.g., videoscopes or surveillance equipment. Examples of such alternative applications are described in co-pending patent application Ser. No. 09/126,368, which is hereby incorporated herein by reference. While other lens assemblies may be capable of achieving similar optical characteristics, such lens assemblies would generally include a greater number of distinct lenses, thus preventing them from being used in devices where it is desirable to minimize the physical dimensions of the lens assembly.

As shown in the illustrative embodiment of FIGS. 10–11, the lens assembly 128 may include a distal lens 1020, a doublet lens 1030 (including component lenses 1030a–b), and a proximal lens 1040. As shown, the lens assembly 128 may also include an outer lens 1010 to further focus light received from a target. The outer lens 1010 may, for example, be formed from a polycarbonate material having a radius of curvature of "5" mm, a thickness of "0.381" mm, and a diameter of "10" mm. In one embodiment, the outer lens 1010 comprises a part of the sheath 316 (FIG. 3). Alternatively, the outer lens 1010 may be housed by the lens housing 1002 of FIG. 10.

In the illustrative embodiment shown, the distal lens 1020 is a convex/concave lens that may be formed, for example, from SFL56 type optical glass having a thickness of "0.53" mm. The convex surface of the distal lens 1020 may have a radius of curvature of "1.3" mm, and the concave surface of the distal lens 1020 may have a radius of curvature of "2.378" mm. When used in conjunction with the outer lens 1010, the lens 1020 may be separated from the outer lens 1010 by a space of "0.3" mm.

In the embodiment of FIGS. 10 and 11, the lens 1030 is a doublet lens including component lenses 1030a–b that are formed from two different types of glass. The lens 1030a may, for example, be formed from SK18A type optical glass having a thickness of "0.919" mm, and the lens 1030b may, for example, be formed from SFL56 type optical glass having a thickness of "0.657" mm. The concave surface of the lens 1030a may, for example, have a radius of curvature of "0.948" mm, and the convex surface of the lens 1030a may, for example, have a radius of curvature "1.052" mm. The concave surface of the lens 1030b may, for example, have a radius of curvature of "1.052" mm (i.e., the same as the convex surface of the lens 1030a), and the convex surface of the lens 1030b may, for example, have a radius of curvature of "1.7162" mm.

The lenses 1030a may be cemented together using an optical cement (e.g., NORLAND 61), and the doublet lens 1030 may be separated from the distal lens 1020, for example, by a distance of "0.533" mm. The distance between the distal lens 1020 and an aperture stop 1125 (see FIG. 11) of the lens assembly 128 (i.e., the plane at which the light rays converge) may, for example, be "0.2" mm, and the distance between the aperture stop 1125 and the doublet lens 1030 may, for example, be "0.333" mm.

In the illustrative embodiment of FIGS. 10–11, the proximal lens 1040 is a bi-convex lens that may be formed, for example, from SK18A type optical glass having a thickness of "1.500" mm. The radius of curvature of each of the convex surfaces of the proximal lens 1040 may, for example, be "6.063" mm. This permits the proximal lens 1040 to be manufactured at a low cost, as similar fabrication procedures can be used for each surface. Furthermore, production of the proximal lens assembly 128 is facilitated and manufacturing defects are reduced because the proximal lens 1040 cannot be inserted in the wrong orientation. That is, when both surfaces of a lens have the same shape (i.e., bi-concave or bi-convex) and differ only in their radius of curvature, it is difficult to distinguish one surface of the lens from the other. In the illustrative embodiment shown, the proximal lens 1040 is separated from the doublet lens 1030 by a space of "0.1" mm, and is separated from image sensor 124 by a space of "0.758" mm. Although not shown in FIGS. 10–11, each of the lenses 1020, 1030 and 1040 may include an anti-reflective coating on its outermost surface.

It should be appreciated that the materials and dimensions of the lens assembly 128 described above are exemplary only, as the dimensions of the lenses 1010, 1020, 1030, 1040, the types of optical glass, and the separation distances between the lenses may be varied. The example glass types given above, i.e., optical glass types SFL56 and SK18A, are available from Schott Glass Technologies, Inc. of Duryea Pa. Optical glass types from other manufacturers may alternatively be used, although other manufacturers may have different designations for optical glass types having similar optical characteristics to those described above. In general, the optical characteristics that are most significant are the index of refraction and the V number (i.e., the ABBE value) of the glass. The polycarbonate material used for the outer lens 1010 may, for example, have an index of refraction of "1.585" and a V number of "29.9," the SFL56 type optical glass may, for example, have an index of refraction of "1.785" and a V number of "26.1," and the SK18A type optical glass may, for example, have an index of refraction of "1.639" and a V number of "55.4." While the particular embodiment of the lens assembly 128 described in connection with FIGS. 10–11 has significant advantages, it should be appreciated that any of numerous other types of lens assemblies having different numbers and/or types of components may alternatively be employed, and that the invention is not limited to the particular embodiment of the lens assembly 128 described above.

In one embodiment of the present invention, the lens assembly 128 is used with an image sensor 124 (e.g., a CCD) that includes one or more optical surfaces 1050, 1060 that are separated from a pixel array 1070 of the image sensor 124 (FIGS. 10–11). An example of such an image sensor 124 is the GPKS 462 model CCD from Panasonic. The optical surfaces 1050, 1060 may include one or more filters (i.e., an infrared filter, an antialiasing filter, etc). The image sensor 124 may also include a plurality of microlenses 1065 that are used to increase the sensitivity of the pixel elements in the pixel array 1070. Such image sensors having microlenses 1065 covering the pixel elements of the pixel array 1070 have become increasingly popular. However, applicants have found that conventional lens systems are not well suited for use with such image sensors. In particular, applicants have determined that when the light incident on the outermost surface of an image sensor (e.g., the surface 1050) is more than approximately ten degrees from perpendicular, the pixel elements of the image sensor can fail to adequately and uniformly image a target. That is, due to the presence of the microlenses 1065, the amount of light detected by the pixel elements at the outer edges of the array can be less than that detected by the pixel elements in the center of the array, even when viewing a uniformly lit target. However, the lens assembly 128 described above is particularly well suited for use with image sensors having such microlenses 1065 covering the pixel array 1070 because the lens assembly 128 focuses light so that it is nearly perpendicular to the outermost surface 1050 of the image sensor 124, even at the outer edges of the image sensor (i.e., the lens assembly is telocentric in image space). It should be appreciated that although the lens assembly 128 is particularly well suited for use with this type of image sensor, the invention in not limited in this respect, and that any of numerous alternative types of image sensors (with or without microlenses 1065 and the other above-described features) may be employed.

Figure 12:
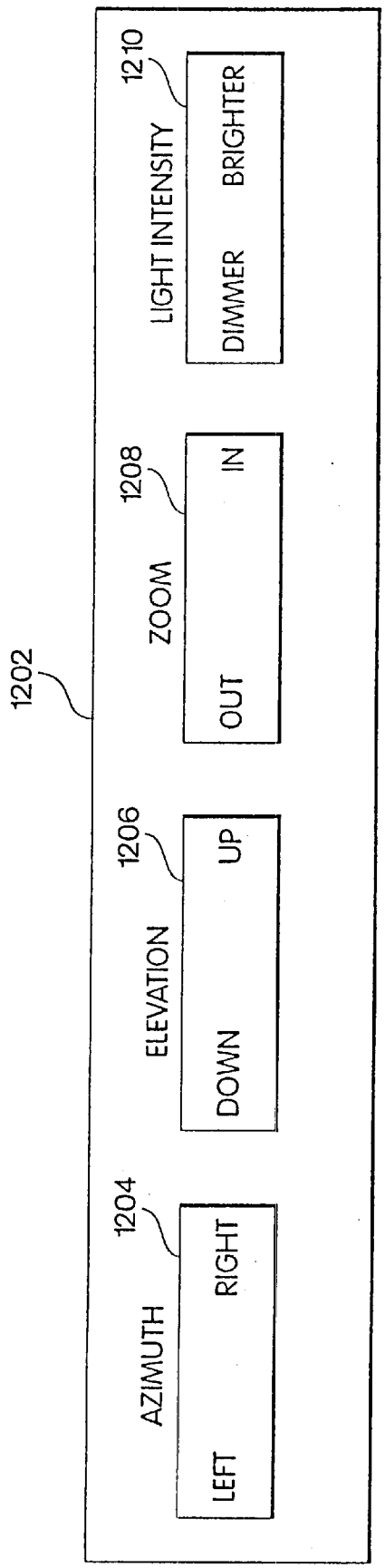
FIG. 12 shows an example of a foot pedal control assembly that may be employed as the camera remote control of FIG. 1 in one embodiment of the invention.

In contrast to conventional scopes that are manually positioned within a remote area to be viewed (e.g., a patient's body cavity), the camera remote-control 108 (FIG. 1) may be used to position the camera head 122 within the cavity from a location outside the cavity. FIG. 12 shows an example of a foot pedal control assembly 1202 that may be employed as the camera remote-control 108. In the illustrative embodiment of FIG. 12, the foot pedal control assembly 1202 includes four controls: (1) an azimuth (left or right) control 1204; (2) an elevation (up or down) control 1206; (3) a zoom (in or out) control 1208; and (4) a light intensity (dimmer or brighter) control 1210. With respect to the azimuth control 1204, the elevation control 1206, and the light intensity control 1210, signals from the foot pedal control assembly 1202 may be routed (via the camera controller 102) to the camera 106 (FIG. 1). If necessary, the camera controller 102 may be used to convert the signals from the foot pedal control assembly 1202 into signals which are suitable to control the actuator(s) 118 and/or the lights 802, 804 within the camera 106. With respect to the zoom control 1208, signals from the foot control assembly 1202 may be used to cause the camera controller 102 to adjust a relative portion of the sensed image that is displayed on the display 104 (i.e., to digitally zoom) so as to adjust the zoom of the displayed image. Alternatively, a mechanical zoom control (not shown), including an additional actuator 118 (not shown) and an additional mechanical link 132 (not shown), may be provided in the camera 106 to mechanically adjust a zoom of the camera head 122 in response to signals from the camera remote-control 108.

Figure 13:
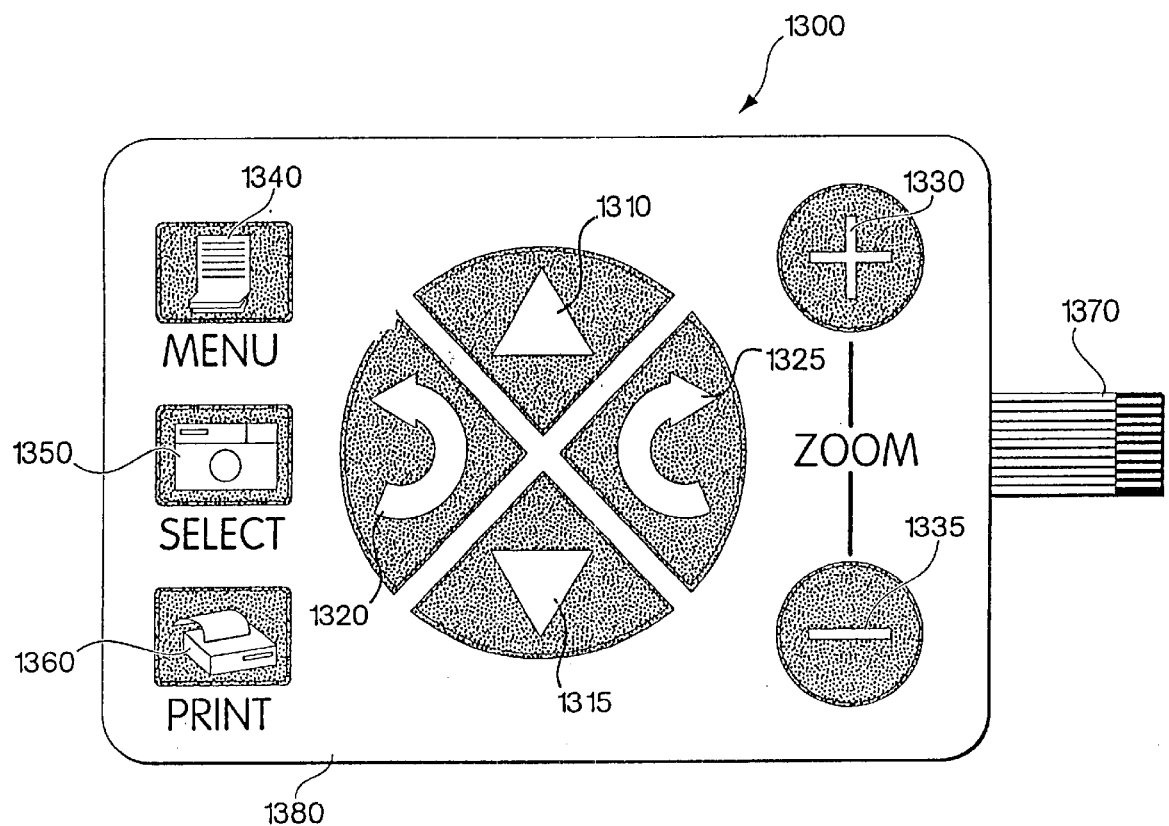
FIGS. 13–15 show an example of a hand-operated remote control that may be employed as the camera remote control of FIG. 1 in accordance with another embodiment of the invention.
Figure 14:
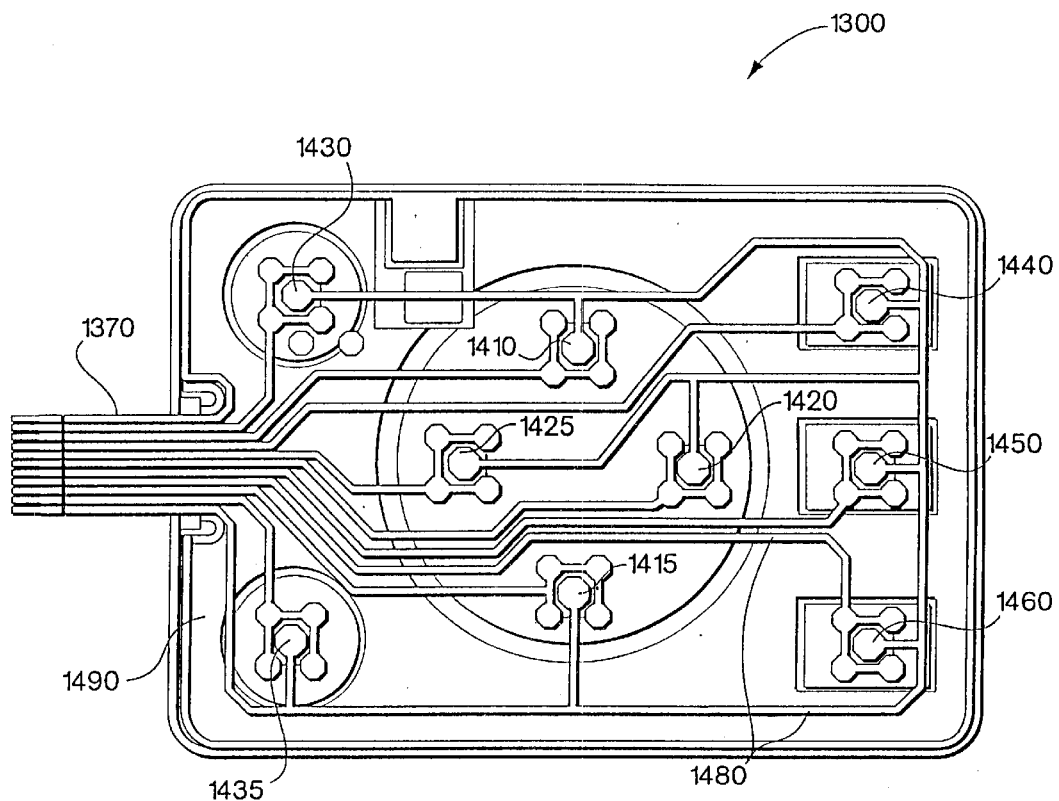
Figure 15:
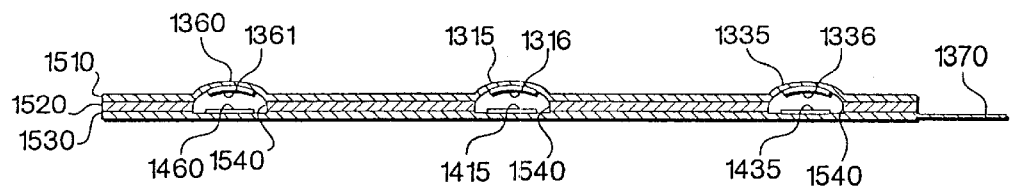

FIGS. 13–15 (in several different views) show an example of another remote-control device, i.e., a hand operated remote-control touch panel 1300, which may be used as the camera remote-control 108. In one embodiment for use in surgical applications, the remotecontrol touch panel 1300 is constructed from medical-grade plastic that is provided in a sterilized condition, and is intended to be disposed of after use. However, it should be appreciated that the remote-control touch panel 1300 may alternatively be constructed from other materials, such as heat-resistant materials that allow it to be sterilized and re-used.

As shown in FIG. 13, the remote-control touch panel 1300 may include a number of controls 1310–1360 for controlling the camera 106. Each of these controls provides a control signal that can be communicated to the camera controller 102, for example, by a wire that is connected to lead 1370. Alternatively, a wireless transmission medium (not shown) can be used to communicate the control signals to the camera controller 102. In the example shown, controls 1310 and 1315 adjust the elevation of the camera head 122, and controls 1320 and 1325 adjust the azimuth of the camera head 122. Also, in the FIG. 13 embodiment, controls 1330 and 1335 alter the field of view 704 (FIG. 7) of the camera head by zooming in and out on the target 714 being imaged.

In the embodiment depicted, each of controls 1310–1335 can be activated by depressing a raised button on an upper surface 1380 of the touch panel. Because each button is raised above the plane of the touch panel 1300, the person operating the camera 106 can control the camera using only their sense of touch. This form of tactile feedback enables the operator (e.g., a surgeon) to focus his or her full attention on the procedure being performed. Furthermore, each button can also include raised lettering on the top surface of the button to further aid selection by the operator.

As shown in FIG. 13, the remote-control touch panel 1300 also includes controls 1340–1360 for use in conjunction with a computerized control mechanism (e.g., the camera controller 102) to manipulate and/or store the signals from the image sensor 124. As described further below, menu control 1340 enables the operator to select and adjust control parameters that affect the quality of the image being displayed. The control 1350 enables the operator to store one or more snapshots of an image seen by the image sensor at a particular instant in time. For example, snapshots of the image can be stored by the memory 114 (FIG. 1), which may comprise any form of storage medium (i.e., disk, tape, compact disk, etc.). The control 1360 can be used to cause the printer 116 to print a snapshot of an image seen by the image sensor 124 at a particular instant of time, or to print a copy of an image that has been previously stored in the memory 114.

As noted above, menu control 1340 may enable the operator (e.g., a surgeon) to control the quality of the image being displayed through a series of pop-up menus that are displayed on a display device (e.g., the display 104). For example, when the menu control 1340 is selected, a top level menu may be displayed that allows the operator to manipulate the nature of the picture being displayed, for example, by altering the brightness, contrast, tint, color, etc. Controls 1310 and 1315 can be used to scroll up and down the top-level menu, and control 1350 can be used to select a particular sub-menu from the top-level menu. Upon selection of a particular sub-menu, controls 1320 and 1325 may be used to increase and decrease the value of a particular display parameter, for example, the contrast of the image. Menu control 1340 may also be used to permit the operator to select a predefined set of preferred display parameters, or to enable the operator to take advantage of the capabilities of the camera controller 102 by performing other functions (e.g., transmitting an image captured by the system over a transmission line (not shown) coupled to the camera controller 102).

In the embodiment shown in FIGS. 13–15, the remote-control touch panel 1300 is formed from three layers of medical-grade plastic including an upper layer 1510, a lower layer 1530, and an intermediate layer 1520. In the example shown, the upper layer 1510 includes a plurality of conductive contacts (e.g., 1361, 1316, 1336) corresponding to the plurality of controls 1310–1360. In the lower layer 1530, directly below each of these conductive contacts, is a corresponding contact (e.g. 1460, 1415, 1435) that is connected to lead 1370 by a respective one of conductors 1480 (FIG. 14). Intermediate layer 1520 separates the conductive contacts in the upper layer 1510 from their corresponding contacts 1410–1460 in lower layer 1530. However, apertures 1540 in the intermediate layer 1520 permit electrical conduction between each set of corresponding contacts in the upper and lower layers when the corresponding control is depressed or activated.

In the embodiment shown in FIGS. 13–15, the lead 1370 may be integrally formed as part of the lower layer 1530. This can simplify the manufacture of the remote-control touch panel by reducing the number of distinct elements in the design. Furthermore, as fewer distinct elements need to be aligned (i.e., each of conductors 1480 with one of the conductors in lead 1370) to form the touch panel, the cost of manufacturing the touch panel can be reduced, thereby allowing it to be economically disposed of after use.

In one embodiment of the present invention, the lower surface 1490 (FIG. 14) of the touch panel is coated with an adhesive and covered by a removable backing (not shown). Removal of the backing permits the touch panel to be mounted to a supporting surface, such as an operating table, or the patient. In this manner, the remote-control touch panel 1300 can be positioned where it is most conveniently used. Furthermore, because the remote-control touch panel 1300 is formed from flexible materials, the touch panel can be mounted to irregularly shaped surfaces as well as planar surfaces.

It should further be appreciated that the remote-control touch panel 1300 in which the camera head 122 is positionable by the operator's hands provides a number of advantages. For example, when used by a surgeon, the remote-control touch panel can be mounted so that it is within the field of view of the surgeon during the surgical procedure. In addition, it can be mounted so that it is close to the surgeon's hand during all phases of the surgical procedure.

Figure 16:
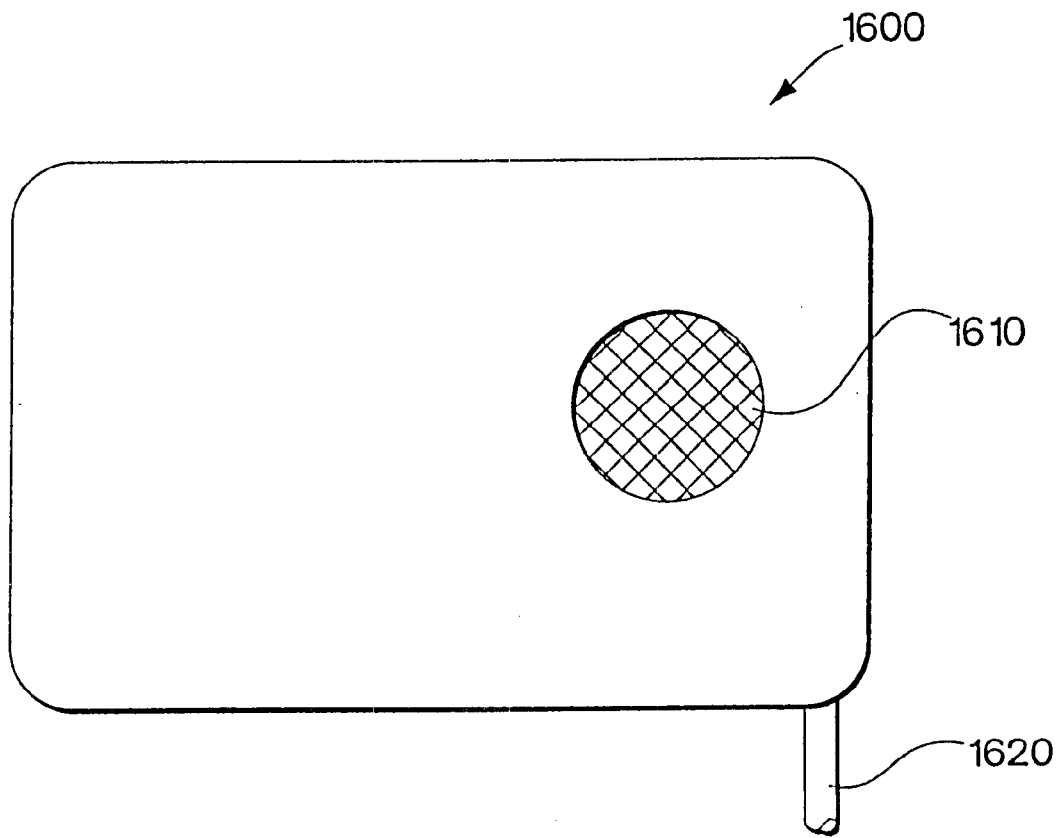
FIG. 16 shows an example of a voice-activated remote-control that may be employed as the camera remote-control of FIG. 1 in accordance with yet another embodiment of the invention.

FIG. 16 shows yet another example of a camera remote-control 108, i.e., a voice-activated remote-control 1600, which may be used to remotely control the camera 106. In the illustrative embodiment shown, the voice-activated remote-control 1600 includes a microphone 1610 which is coupled to the camera controller 102 via a cable 1620. Alternatively, the voice activated remote-control 1600 may be coupled to the camera controller 102 via a wireless transmission medium.

Voice recognition software stored on the memory 114 may be executed by the processor 110 in the camera controller 102 to control the operation of the camera 106 in response to predefined oral commands. For example, the words "left" and "right" can be used to alter the azimuth of the camera head 122, while the words "up" and "down" can be used to alter the elevation of the camera head 122. Other commands may also be defined to adjust the field of view of the camera (e.g., "zoom in," "zoom out"), adjust the intensity of the lights (e.g., "bright," "dim"), and to store or print a picture. In this manner, the operator (e.g., a surgeon) can devote his/her full attention to the procedure being performed, as neither the operator's hands nor eyes are required to control the operation of the camera 106.

Regardless of the particular type of remote-control device that is used as the camera remote-control 108, the camera remote-control 108 may (as discussed above) be spaced apart from the camera 106, providing great flexibility in the placement of the camera remote-control 108. That is, the camera remote-control 108 may be positioned away from the camera 106 and/or the camera controller 102 at a location where it can be most conveniently accessed by the operator. In one embodiment, the camera remote-control 108 includes an adhesive backing that permits it to be mounted to any supporting surface, including a patient, that is convenient to the operator. Alternatively, the camera remote-control 108 may be mounted to another device (e.g., a medical instrument) where it can be conveniently accessed while using the other device.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A camera comprising:
   an elongated sheath having an inner surface, the sheath defining a longitudinal axis;
   an image sensor having an imaging axis; and
   a support, at least partially disposed within the sheath, that supports the image sensor within the sheath such that the image sensor is rotatable about at least two axes of rotation, the image sensor being rotatable about at least one of the axes through a range of orientations including a position greater than 90 degrees from the longitudinal axis, and wherein the imaging axis is oriented normal to the inner surface of the sheath throughout at least a portion of the image sensor's range of orientations.

2. The camera of claim 1, wherein the range of orientations includes a position of 135 degrees from the longitudinal axis.

3. The camera of claim 1, wherein the image sensor is disposed adjacent a distal end of the sheath.

4. The camera of claim 1, wherein the sheath is rigid.

5. The camera of claim 1, wherein the support is arranged to rotate the image sensor through at least ninety degrees about each of its at least two axes of rotation.

6. The camera of claim 1, further including a housing including at least one actuator, the housing being attached to the sheath and the at least one actuator being mechanically coupled to the image sensor to rotate the image sensor about at least one of its at least two axes of rotation.

7. The camera of claim 6, wherein the at least one actuator includes a pair of actuators, each of the pair of actuators being mechanically coupled to the image sensor to rotate the image sensor about a respective one of its at least two axes of rotation.

8. The camera of claim 7, wherein the support has a longitudinal axis that extends along a length of the sheath, and wherein one of the at least two actuators is arranged to rotate the support about the longitudinal axis of the support.

9. The camera of claim 6, wherein the imaging axis of the image sensor passes through different portions of the sheath when the position of the imaging axis is adjusted by the at least one actuator.

10. The camera of claim 1, wherein the support has a longitudinal axis that extends along a length of the sheath, and wherein the support is rotatable within the sheath about the longitudinal axis of the support.

11. An endoscope, comprising:
    a camera housing;
    an image sensor disposed within the camera housing, the image sensor being rotatable about at least two axes of rotation within the camera housing; and
    an actuation module removably attached to the camera housing, the actuation module comprising a module base removably mounted to the camera housing, and a pair of actuators mounted to the module base so that the pair of actuators can be removed from and coupled to the camera housing as a single unit, each of the pair of actuators being adapted to rotate the image sensor about a respective one of the at least two axes of rotation.

12. The camera of claim 11, wherein the camera includes an elongated sheath in which the image sensor is disposed such that an imaging axis of the image sensor passes through a distal end of the elongated sheath.

13. The camera of claim 12, wherein the camera housing includes an upper housing attached to a proximal end of the elongated sheath, and wherein the module base is adapted to be removably mounted in the upper housing.

14. The camera of claim 11, further comprising a camera module, the camera module comprising:
    a camera module base removably mounted to the camera housing;
    the image sensor being mounted to the camera module base;
    a cable mounted to the camera module base and coupled to the image sensor; and
    a signal conditioning circuit mounted to the camera module base and coupled to the cable to receive an electronic signal produced by the image sensor via the cable;
    whereby the image sensor, the cable, the signal conditioning circuit, and the camera module base are removable from and attachable to the camera housing as a single unit.

15. A camera comprising:
    an elongated sheath having an inner surface, the sheath defining a longitudinal axis;
    an image sensor having an imaging axis; and
    a support, at least partially disposed within the sheath, that supports the image sensor within the sheath such that the image sensor is rotatable about at least two axes of rotation, the image sensor being rotatable about at least one of the axes through a range of orientations including a position up to 165 degrees from the longitudinal axis, and wherein the imaging axis is oriented normal to the inner surface of the sheath throughout at least a portion of the image sensor's range of orientations.

* * * * *